United States Patent [19]
Holt et al.

[11] Patent Number: 5,641,765
[45] Date of Patent: Jun. 24, 1997

[54] 17-α AND 17-β SUBSTITUTED ACYL-3-CARBOXY-3,5-DIENES AND USE IN INHIBITING 5-α-REDUCTASE

[75] Inventors: Dennis Alan Holt, Stow, Mass.; Mark Alan Levy, Wayne, Pa.

[73] Assignee: SmithKline Beecham Corporation, King of Prussia, Pa.

[21] Appl. No.: 436,240

[22] PCT Filed: Nov. 18, 1993

[86] PCT No.: PCT/US93/11241

§ 371 Date: May 17, 1995

§ 102(e) Date: May 17, 1995

[87] PCT Pub. No.: WO94/11386

PCT Pub. Date: May 26, 1994

[30] Foreign Application Priority Data

Nov. 18, 1992 [GB] United Kingdom ............ 9224213
Aug. 14, 1993 [GB] United Kingdom ............ 9316954

[51] Int. Cl.⁶ .................. A61K 31/375; C07J 9/00
[52] U.S. Cl. ............ 514/169; 514/171; 552/610; 552/557; 552/553; 552/548; 552/540; 552/502
[58] Field of Search ............ 514/169, 172; 552/502, 540, 548, 553, 557, 610

[56] References Cited

U.S. PATENT DOCUMENTS

| | | | |
|---|---|---|---|
| 4,055,603 | 10/1977 | Johnson et al. | 552/610 |
| 4,954,446 | 9/1990 | Holt et al. | 435/184 |
| 5,017,568 | 5/1991 | Holt et al. | 514/173 |
| 5,032,586 | 7/1991 | Metcalf et al. | 514/177 |
| 5,041,433 | 8/1991 | Holt et al. | 514/176 |
| 5,137,882 | 8/1992 | Holt et al. | 514/182 |
| 5,196,411 | 3/1993 | Rasmusson et al. | 514/169 |
| 5,212,166 | 5/1993 | Panzeri et al. | 514/176 |
| 5,446,225 | 8/1995 | Trost et al. | 585/359 |

FOREIGN PATENT DOCUMENTS

| | | |
|---|---|---|
| 0 343 954 | 11/1989 | European Pat. Off. . |
| 0 465 123 A2 | 1/1992 | European Pat. Off. . |
| 0 567 271 A2 | 10/1993 | European Pat. Off. . |
| WO93/22333 | 11/1993 | European Pat. Off. . |
| WO93/14106 | 1/1993 | WIPO . |
| WO93/16097 | 2/1993 | WIPO . |
| WO93/16098 | 2/1993 | WIPO . |
| WO94/11385 | 5/1994 | WIPO . |

OTHER PUBLICATIONS

J. Med. Chem. 33, pp. 943–950 (1990).
J. Med. Chem. 33, pp. 937–942 (1990).
Biochemistry, vol. 29, No. 11, pp. 2815–2830 (1990).

*Primary Examiner*—Kimberly J. Prior
*Assistant Examiner*—Deborah Lambkin
*Attorney, Agent, or Firm*—Wayne J. Dustman; Charles M. Kinzig; Edward T. Lentz

[57] ABSTRACT

Invented are 17α and 17β-substituted acyl-3-carboxy-3,5-diene analogues of steroidal synthetic compounds, pharmaceutical compositions containing these compounds, and methods for using these compounds to inhibit steroid 5-α-reductase. Also invented are intermediates and processes used in preparing these compounds.

19 Claims, No Drawings

17-αAND 17-βSUBSTITUTED ACYL-3-CARBOXY-3,5-DIENES AND USE IN INHIBITING 5-α-REDUCTASE

This application is a 371 of PCT/US93/11241 filed Nov. 18, 1993.

FIELD OF THE INVENTION

The present invention relates to certain novel 17α and 17β substituted acyl-3-carboxy 3,5-diene steroidal compounds, pharmaceutical compositions containing these compounds, and methods for using these compounds to inhibit steroid 5-α-reductase. Also invented are novel intermediates and processes useful in preparing these compounds.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective control results in excessive androgen hormone production. For example, acne vulgaris, seborrhea, female hirsutism, male pattern baldness and prostate diseases such as benign prostatic hypertropy are correlated with elevated androgen levels. Additionally, the reduction of androgen levels has been shown to have a therapeutic effect on prostate cancer.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone thus serves as a prohormone for dihydrotestosterone (DHT), its 5-α-reduced analogue, in these tissues but not in others such as muscle and testes. Steroid 5-α-reductase is a Nicotinamide Adenine dinucleotide Phosphate(NADPH)dependent enzyme that converts testosterone to DHT. The importance of this enzyme in male development was dramatically underscored by the discovery of a genetic steroid 5-α-reductase deficiency in male pseudohermaphrodites. Imperato-McGinley, J., et al., (1979), *J. Steroid Biochem.* 11:637–648.

Recognition of the importance of elevated DHT levels in various disease states has stimulated many efforts to synthesize inhibitors of this enzyme. Among the most potent inhibitors identified to date are 3-carboxy-androsta-3,5-diene steroidal derivatives.

A number of 5-α-reductase inhibitors are known in the art. For example,

1. *Bioinorganic Chemistry*, 17, pp. 372–376 (1986), by B. W. Metcalf, et al. describes the inhibition of human steroid 5α reductase (EC 1.3.1.30) by 3 androstene-3-carboxylic acids;
2. *Biochemistry* (1990) Vol. 29, pp. 2815–2824, by M. A. Levy, et al, M. A. Levy, et al. describes the mechanism of enzyme inhibitor interation in the inhibition or rat liver steroid 5α reductase by 3-androstene-3-carboxylic acids;
3. *J. Med. Chem.* (1990) Vol. 33, pp. 943–950 (1990), by D. A. Holt, et al, describes the inhibition of steroid 5α reductase by unsaturated 3-carboxysteroids;
4. *J. Steroid Biochem*, Vol. 34, Nos. 1–6, pp. 571–575 (1989), by M. A. Levy, et al, describes the interaction mechanism between rat prostatic steroid 5-alpha reductase and 3-carboxy-17β-substituted steroids;
5. *J. Med. Chem.* (1990) Vol. 33, pp. 937–942, by D. A. Holt, et al, describes the new steroid class of A ring aryl carboxylic acids;
6. *TIPS* (December 1989) Vol. 10, pp. 491–495, by D. W. Metcalf, et al, describes the effect of inhibitors of steroid 5α reductase in benign prostatic hyperplasia, male pattern baldness and acne; and
7. EPO Publn. No. 0 289 327, to D.A. Holt, et al. (SmithKline Beckman) describes steroidal 3-carboxylic acid derivatives as useful 5α reductase inhibitors.
8. EPO Publn. No. 0 343 954 A3, to D.A. Holt, et al., (SmithKline Beckman) describes steroidal 3-carboxylic acid derivatives as useful 5-α-reductase inhibitors.
9. EPO Publn. No. 0 465 142 A1, to G. H. Rasmusson, et al, (Merck & Co. Inc.) describes steroidal 3-carboxylic acid derivatives as useful 5α-reductase inhibitors.

However, none of the above references specifically suggest that any of the novel steroidal 17α or 17β-substituted acyl-3-carboxy-androsta-3,5-diene compounds of the present invention would have utility as potent testosterone 5-α-reductase inhibitors.

SUMMARY OF THE INVENTION

This invention relates to a compound of the formula I:

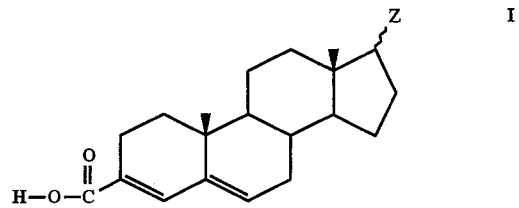

wherein

Z is α or β

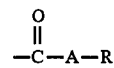

in which

A is a linear or branched, saturated or unsaturated hydrocarbon chain containing from 1–12 carbon atoms: and R is substituted alkyl, cycloalkyl or aryl where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where R$^6$ is hydrogen or alkyl, n is 0–2 and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl;

b) cycloalkyl is nonaromatic, unsaturated or saturated, cyclic or polycyclic C$_3$–C$_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; and c) aryl is cyclic or polycyclic aromatic C$_3$–C$_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, C$_6$–C$_{12}$aryl, alkoxy, acyloxy, substituted C$_6$–C$_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; and pharmaceutically acceptable salts, hydrates, solvates and esters thereof.

The invention also is a method for inhibiting 5-α-reductase activity in mammals, including humans, that comprises administering to a subject an effective amount of a presently invented 5-α-reductase inhibiting compound. In a further aspect of the invention there are provided novel intermediates and novel processes useful in preparing the presently invented 5-α-reductase inhibiting compounds.

Included in the present invention are pharmaceutical compositions comprising a pharmaceutical carrier and compounds useful in the methods of the invention. Also included in the present invention are methods of co-administering the presently invented 5-α-reductase inhibiting compounds with further active ingredients.

DETAILED DESCRIPTION OF THE INVENTION

The compounds of this invention that inhibit 5-α-reductase have the following Formula (I):

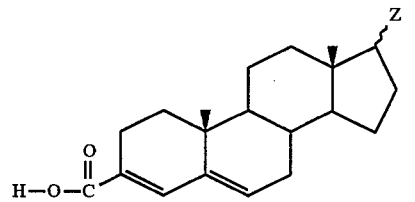

wherein

Z is α or β

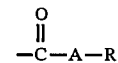

in which

A is a linear or branched, saturated or unsaturated hydrocarbon chain containing from 1–12 carbon atoms; and R is substituted alkyl, cycloalkyl or aryl where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where R$^6$ is hydrogen or alkyl, n is 0–2 and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR$^6$, —S(O)$_n$R$^7$, nitro, cyano, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl;

b) cycloalkyl is nonaromatic, unsaturated or saturated, cyclic or polycyclic C$_3$–C$_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromntic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and pharmaceutically acceptable salts, hydrates, solvates and esters thereof.

Preferred among the presently invented Formula (I) compounds are those in which A is a linear or branched, saturated or unsaturated hydrocarbon chain containing from 2–12 carbon atoms.

Preferred among the presently invented compounds are those having the following Formula (II):

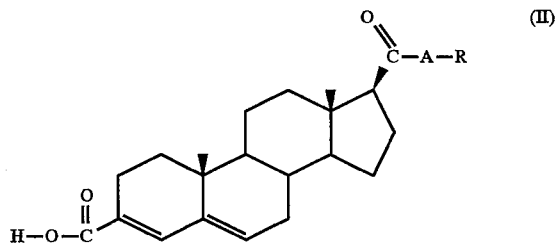

in which

A is a linear or branched, saturated or unsaturated hydrocarbon chain containing from 1–12 carbon atoms: and R is substituted alkyl, cycloalkyl or aryl where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR$^6$ and —S(O)$_n$R$^5$, where $R^6$ is hydrogen or alkyl, n is 0–2 and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, amino; N-acylamino, oxo, hydroxy, cycloalkyl, substituted cycloalkyl, aryloxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cyclalkyl, substituted $C_6$–$C_{12}$aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, —C(O)OR$^6$, —S(O)$_n$R$^7$, nitro, cyano, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where $R^6$ is hydrogen or alkyl, n is 0–2 and $R^7$ is hydrogen or alkyl; and pharmaceutically acceptable salts, hydrates, solvates and esters thereof.

Preferred among the presently invented Formula II compounds are those in which A is a linear or branched, saturated or unsaturated hydrocarbon chain containing from 2–12 carbon atoms.

Preferred among the presently invented Formula II compounds are those in which A is a linear or branched, saturated or unsaturated hydrocarbon chain containing from 1–6 carbon atoms and R is a) a linear or branched, saturated or unsaturated hydrocarbon chain containing 1–12 carbon atoms substituted with one or more substituents selected from the group consisting of —O$_6$–C$_{12}$aryl, carboxy, —OC$_1$C$_4$alkyl, halogen and —S(O)$_n$R$^7$, where n is 0–2 and $R^7$ is hydrogen or C$_{1-4}$alkyl;

b) C$_3$–C$_8$ nonaromatic, unsaturated or saturated, cycloalkyl, optionally substituted with one or more substituents selected from the group consisting of: —OC$_6$–C$_{12}$aryl, —(CH$_2$)$_m$OH, —OC$_1$–C$_4$alkyl, C$_6$–C$_{12}$aryl, C$_1$–C$_4$alkyl, trifluoromethyl, halogen, —(CH$_2$)$_p$COOH, —S(O)$_n$R$^7$ and protected —OH, where m is 0–4, p is 0–3, n is 0–2 and $R^7$ is hydrogen or C$_{1-4}$alkyl; or c) C$_4$–C$_{12}$aryl, optionally containing one or more heteroatoms, provided that when C is 4 the aromatic ring contains at least one heteroatom, and optionally substituted with one or more substituents selected from the group consisting of: —OC$_6$–C$_{12}$aryl, —(CH$_2$)$_m$OH, C$_6$–C$_{12}$aryl, C$_1$–C$_4$alkyl , —OC$_1$–C$_4$ alkyl, trifluoromethyl, halogen, —(CH$_2$)$_p$COOH, —S(O)$_n$R$^7$ and protected —OH, where m is 0–4, p is 0–3, n is 0–2 and $R^7$ is hydrogen or C$_{1-4}$alkyl; and pharmaceutically acceptable salts, hydrates, solvates and esters thereof.

Preferred among said Formula II compounds are those in which A is a linear or branched, saturated or unsaturated hydrocarbon chain containing from 2–6 carbon atoms.

Particularly preferred among Formula II compounds are those in which A is a linear or branched, saturated or unsaturated hydrocarbon chain containing from 1–4 carbon atoms and R is a) a linear or branched hydrocarbon chain containing 1–6 carbon atoms substituted with one or more halogens, b) C$_3$–C$_8$ nonaromatic, unsaturated or saturated cycloalkyl, optionally substituted with one or more substituents selected from the group consisting of: halogen, thio, methylsulfonyl, methylsulfoxyl, methylthio, carboxy, hydroxy, trifluoromethyl, phenoxy and methoxy or c) C$_4$–C$_{12}$aryl, optionally containing one more heteroatoms, provided that when C is 4 the aromatic ring contains at least one heteroatom, and optionally substituted with one or more substituents selected from the group consisting of: halogen, thio, methylsulfonyl, methylsulfoxyl, methylthio, carboxy, hydroxy, trifluoromethyl, phenoxy and methoxy and pharmaceutically acceptable salts, hydrates, solvates and esters thereof.

Preferred among said Formula II compounds are those in which A is a linear or branched, saturated or unsaturated hydrocarbon chain containing from 2–4 carbon atoms.

Particularly preferred among Formula II compounds are those in which A is a linear or branched, saturated or unsaturated hydrocarbon chain containing from 1–4 carbon atoms and R is a) CF$_3$ b) C$_5$–C$_7$ cycloalkyl or c) C$_4$–C$_{12}$ aryl, optionally containing one or more heteroatoms, provided that when C is 4 the aromatic ring contains at least one heteroatom, and optionally substituted with one or more substituents selected from the group consisting of: halogen, thio, methylsulfonyl, methylsulfoxyl, methylthio, carboxy, hydroxy, trifluoromethyl, phenoxy and methoxy and pharmaceutically acceptable salts, hydrates, solvates and esters thereof.

Preferred among said Formula II compounds are those in which A is a linear or branched, saturated or unsaturated hydrocarbon chain containing from 2–4 carbon atoms.

Particularly preferred among formula II compounds are:

17β-(phenylpropylcarbonyl)-androsta-3,5-diene-3-carboxylic acid,

17β-(benzylcarbonyl)-androsta-3,5-diene-3-carboxylic acid,

17β-(cydohexylethylcarbonyl)-androsta-3,5-diene-3-carboxylic acid,

17β-(phenethylcarbonyl)-androsta-3,5-diene-3-carboxylic acid,

17β-(5,5,5-trifluoro-1-oxopentyl)-androsta-3,5-diene-3-carboxylic acid,

17β-(2-cyclohexyl-1-oxoethyl)-androsta-3,5-diene-3-carboxylic acid,

17β-(3 -methyl-3-phenyl-1-oxobutyl)-androsta-3,5 -diene-3-carboxylic acid,

17β-(3-(4-methoxy phenyl)-1-oxopropyl)-androsta-3,5-diene-3-carboxylic acid,

17β-(3-(4-hydroxy phenyl)-1-oxopropyl)-androsta-3,5-diene-3-carboxylic acid,

17β-(4-fluorophenethylcarbonyl)-androst-3,5-diene-3-carboxylic acid and

17β-(2,6-difluorobenzylcarbonyl)-androsta-3,5-diene-3-carboxylic acid and pharmaceutically acceptable salts, hydrates, solvates and esters thereof.

The term "α", as used herein, follows standard chemical terminology and means down or that the corresponding substituent is attached below the plane of the paper.

The term "β", as used herein, follows standard chemical terminology and means up or that the corresponding substituent is attached above the plane of the paper.

By the term "protected hydroxy" or "protected —OH" as used herein, is meant the alcoholic or carboxylic -OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like.

As used herein $C_x$–$C_y$ is meant a moiety having from x to y carbons.

By the term "aryl" as used herein, unless otherwise defined, is meant cyclic or polycyclic aromatic $C_3$–$C_{12}$, optionally containing one or more heteroatoms, provided that when C is 3 the aromatic ring contains at least two heteroatoms and when C is 4 the aromatic ring contains at least one heteroatom, and optionally substituted with one or more substituents selected from the group consisting of: alkyl, $C_6$–$C_{12}$ aryl, substituted cycloalkyl, substituted $C_6$–$C_{12}$aryl, aryloxy, hydroxy, alkoxy, cycloalkyl, acyloxy, amino, N-acylamino, nitro, cyano, halogen, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^6$, —S(O)$_n$R$^7$, aryloxy, nitro, cyano, halogen, and protected —OH, where R$^6$ is hydrogen or alkyl, n is 0–2, R$^7$ is hydrogen or alkyl and R$^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where R$^6$ is hydrogen or alkyl, n is 0–2 and R$^7$ is hydrogen or alkyl.

Examples of aryl and substituted aryl substituents as used herein include: phenyl, naphthyl, furanyl, biphenyl, hydroxyphenyl, pyridyl, fluorophenyl, dihydroxyphenyl, methylenedioxyphenyl, dimethylhydroxyphenyl, methoxyphenyl, trifluoromethylphenyl carboxymethylphenyl, phenoxyphenyl, methylsulfonylphenyl, methylthiophenyl, difluorophenyl, carboxyphenyl, methylsulfoxylphenyl and thiophenyl.

Preferred examples of aryl and substituted aryl substituents as used herein include: phenyl, 4-fluorophenyl, 2,6-difluorophenyl, 1-naphthyl, 4-biphenyl, 4-methoxyphenyl, 4-phenoxyphenyl, 4-trifluoromethylphenyl, 4-methylsulfonylphenyl, 4-methylthiophenyl, 3,5-difluorophenyl, 4-hydroxyphenyl, 4-carboxyphenyl, 2-furanyl, 4-methylsulfoxylphenyl, 3-thiophenyl, 2-pyridyl, 3-pyridyl, 4-pyridyl and 3,4-methylenedioxyphenyl.

By the term "$C_6$–$C_{12}$ aryl" as used herein, unless otherwise defined, is meant phenyl, naphthyl, 3,4-methylenedioxyphenyl, pyridyl, or biphenyl.

By the term "substituted" as used herein, unless otherwise defined, is meant that the subject chemical moiety has one or more substituents selected from the group consisting of: hydroxyalkyl, alkoxy, acyloxy, alkyl, amino, N-acylamino, hydroxy, —(CH$_2$)$_g$C(O)OR$^6$, —S(O)$_n$R$^7$, nitro, cyano, halogen, trifluoromethyl and protected —OH, where g is 0–6, R$^6$ is hydrogen or alkyl, n is 0–2, and R$^7$ is hydrogen or alkyl.

By the term "alkoxy" as used herein is meant —Oalkyl where alkyl is as described herein including —OCH$_3$ and —OC(CH$_3$)$_2$CH$_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —OC(O)CH$_3$, —OC(O)CH(CH$_3$)$_2$ and —OC(O)(CH$_2$)$_3$CH$_3$.

By the term "N-acylamino" as used herein is meant —N(H)C(O)alkyl, where alkyl is as described herein.

Examples of N-acylamino substituents as used herein include: —N(H)C(O)CH$_3$, —N(H)C(O)CH(CH$_3$)$_2$ and —N(H)C(O)(CH$_2$)$_3$CH$_3$.

By the term "aryloxy" as used herein is meant —OC$_6$–C$_{12}$aryl where C$_6$–C$_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifluoromethyl, acyloxy, amino, N-acylamino, hydroxy, —(CH$_2$)$_g$C(O)OR$^6$, —S(O)$_n$R$^7$, nitro, cyano, halogen and protected —OH, where g is 0–6, R$^6$ is hydrogen or alkyl, n is 0–2 and R$^7$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$–$C_{12}$ carbon atoms. Examples of alkyl substituents as used herein include: —CH$_3$, —CH$_2$—CH$_3$, —CH$_2$—CH$_2$—CH$_3$, —CH(CH$_3$)$_2$, —C(CH$_3$)$_3$, —(CH$_2$)$_3$—CH$_3$, CH$_2$—CH(CH$_3$)$_2$ and —CH(CH$_3$)—CH$_2$—CH$_3$, —CH=CH$_2$.

By the term "treating" and derivatives thereof as used herein, is meant prophylatic or therapeutic therapy.

By the term "metal-catalyzed coupling reaction" as used herein is meant that the prepared 3-trifluoromethyl sulfonylate or 3-fluorosulfonylate compound is reacted in a suitable organic solvent; preferably dimethylsulfoxide, toluene, dichloroethane, dimethylformamide or THF; with a base, preferably a tertiaryamine base such as triethylamine, pyridine or tributylamine; a $C_1$–$C_6$ alcohol (when an ester is desired) or a $C_1$–$C_6$ carboxylic acid salt, preferably KOAc (when an acid is desired) and a phosphine, such as bis (diphenylphosphino)alkane, preferably 1,3 bis (diphenylphosphino)propane, tri-o-tolyphosphine or 1,1-bis (diphenylphosphino)ferrocene (dppf)) and a metal catalyst, preferably a palladium catalyst such as palladium (II) acetate or palladium (II) chloride or bis(triphenylphosphine) palladium II acetate, thereby forming a metalated complex, and subsequently adding a coupling reagent.

By the term "coupling reagent" as used herein is meant a compound which is capable of reacting with said metalated complex to form an ester or a carboxylic acid substituent. Carbon monoxide is a preferred coupling reagent which when added to the metal-catalyzed coupling reaction, as described herein, yields the desired ester or carboxylic acid group.

Compounds of Formula (I) and compounds of Formula (V) are included in the phamaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The term "α-receptor antagonist", as used herein, refers to a known class of alpha-andrenergic receptor antagonist compounds, such as described in Lafferty, et al. U.S. Pat. No. 4,963,547, which are utilized in treating vascular disorders such as diabetes, cardiovascular disease, benign prostatic hypertrophy and ocular hypertension.

Preferred alpha-andrenergic receptor antagonists for use in the compositions and methods of the invention include amsulosin, terazosin, doxazosin, alfuzosin, indoramin, prazosin, 7-chloro-2-ethyl-3,4,5,6-tetrahydro-4-methylthieno[4,3,2-ef][3]-benzazepine and 8-{3-[4-(2-methoxyphenyl)-1-piperazinyl]-propylcarbamoyl}-3-methyl-4-oxo-2-phenyl-4H-1-benzopyran.

By the term "amsulosin" as used herein is meant a compound of the structure

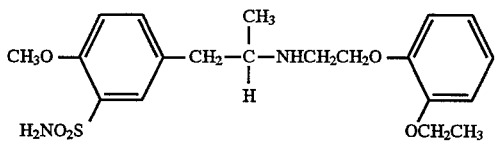

and salts, hydrates and solvates thereof.

Chemically, amsulosin is designated as (−)-(R)-5-[2-[[2-(O-ethoxyphenoxy)ethyl]amino]propyl]-2-methoxybenzenesulfonamide.

Amsulosin is disclosed in U.S. Pat. No. 4,703,063 and claimed in U.S. Pat. No. 4,987,152 as being useful in treating lower urinary tract dysfunction.

By the term "terazosin" as used herein is meant a compound of the structure

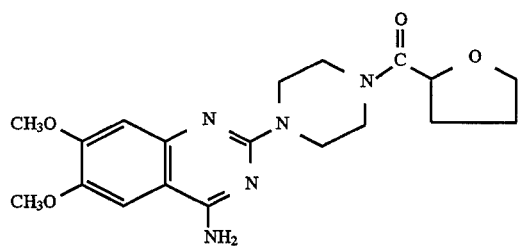

and salts, hydrates and solvates thereof.

Chemically, terazosin is designated as 1-(4-amino-6,7-dimethoxy-2quinazolinyl)-4-[(tetrahydro-2-furoyl)carbonyl]piperazine. Terazosin is disclosed in U.S. Pat. No. 4,251,532.

By the term doxazosin as used herein is meant a compound of the formula

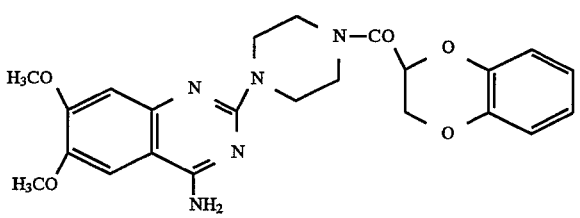

and salts, hydrates and solvates thereof.

Chemically "doxazosin" is designated as 1-(4-amino-6,7-dimethoxy-2-quinazolinyl)-4-[(2,3-dihydro-1,4-benzodioxin-2-yl)carbonyl]-piperazine.

Doxazosin is disclosed in U.S. Pat. No. 4,188,390.

By the term "alfuzosin" as used herein is meant a compound of the formula

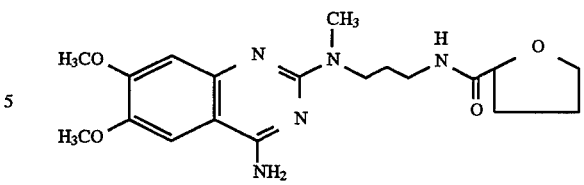

and salts, hydrates and solvates thereof.

Chemically alfuzosin is designated as N-[3-[(4-amino-6,7-dimethoxy-2-quinazolinyl)methylamino]propyl] tetrahydro-2-furancarboxamide.

Alfuzosin is disclosed in U.S. Pat. No. 4,315,007.

By the term "indoramin" as used herein is meant a compound for the formula

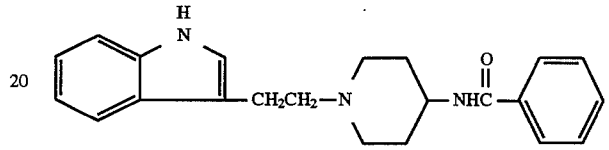

and salts, hydrates and solvates thereof.

Chemically indoramin as designated N-[[1-[2-(1H-indol-3-yl)ethyl]-4-piperidinyl]benzamine.

Indoramin is disclosed in U.S. Pat. No. 3,527,761.

By the term "prazosin" as used herein is meant a compound of the formula

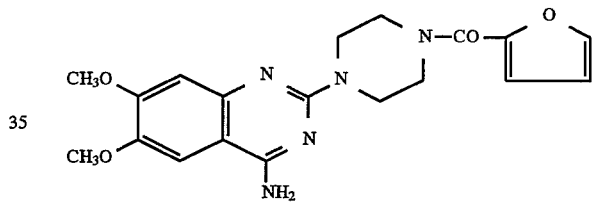

and salts, hydrates and solvates thereof.

Chemically prazosin is designated as 1-(4-amino-6,7-dimethoxy-2-quinazolinyl)-4-(2-furanylcarbonyl)piperazine.

Prazosin is disclosed in U.S. Pat. No. 3,511,836.

"7-chloro-2-ethyl-3,4,5,6-tetrahydro-4-methylthieno[4,3,2-ef][3]benzazepine" as used herein is meant a compound of the structure

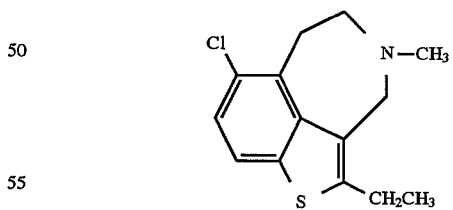

and salts, hydrates and solvates thereof.

7-chloro-2-ethyl-3,4,5,6-tetrahydro4-methylthieno[4,3,2-ef][3]benzazepine is disclosed in U.S. Pat. No. 5,006,521. Additionally, all compounds disclosed in U.S. Pat. No. 5,006,521 as alpha-adrenergic receptor antagonist are preferred alpha-adrenergic receptor antagonist as used herein.

"8-{3-[4-(2-methoxyphenyl)-1-piperazinyl]-propylcarbamoyl}-3-methyl-4-oxo-2-phenyl-4H-1-benzopyran" as used herein is meant a compound of the structure

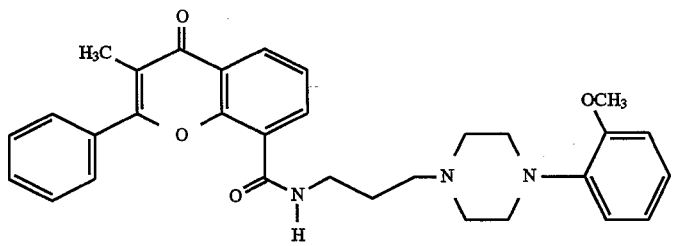

and salts, hydrates and solvates thereof.

8-{3-[4-(9-methoxyphenyl)-1-piperazinyl]-propylcarbamoyl}-3-methyl-4-oxo-9-phenyl-4H-1-benzopyran is disclosed in EPO Publn. No. 0558245 A1, to Leonardi, et al., (Recordati S.A.).

Additionally all compounds disclosed in EPO Publn. No. 0558245 A1, as alpha-adrenergic receptor antagonists are preferred alpha-adrenergic receptor antagonists as used herein.

Persons skilled in the art can readily determine if a compound other than one specifically referred to herein is a alpha-andrenergic receptor antagonist by utilizing the assay described in Lafferty I. Thus, all such compounds are included within the scope of the term "alpha-andrenergic receptor antagonist" as used herein.

By the term "minoxidil" as used herein is meant the compound of the formula:

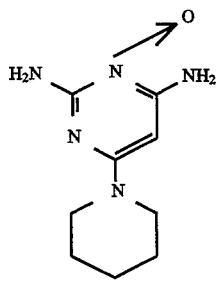

chemically minoxidil is designated as 2,4-pyrimidineadiamine, 6-(1-pipridinyl)-,3-oxide. Minoxidil is the active ingredient in Rogaine® which is sold as topical solution for stimulating hair growth by the Upjohn Company, Kaamazoo, Mich.

The term "aromatase inhibitor", as used herein, refers to a known class of compounds, steroidal and non-steroidal, which prevent the conversion of androgens to estrogens, such as described in Gormley et al. International Publication Number WO 92/18 132. Aromatase inhibitors are disclosed in Gormley et al. as having utility in treating benign prostatic hyperplasia when used in combination with a 5-α-reductase inhibitor.

A preferred aromatase inhibitor for use in the compositions and methods of the invention 4-(5,6,7,8-tetrahydroimidazo-[1,5-α]pyridin-5-yl)benzonitrile (fadrazole). Fadrazole is disclosed in U.S. Pat. No. 4,728, 645. Additionally, all compounds disclosed in Gormley, et al. International Publication No. WO 92/18132 as having aromatase inhibiting activity are preferred aromatase inhibitors as used herein.

As used herein, when a 5-α-reductase inhibitor, as described herein and a further active ingredient or ingredients are utilized together, said 5-α-reductase inhibitor can be co-administered with said further active ingredient or ingredients.

By the term "co-administering" and derivatives thereof as used herein is meant either simultaneous administration or any manner of separate sequential administration of a 5-α-reductase inhibiting compound, as described herein, and a further active ingredient or ingredients, such as other compounds known to treat the disease states of acne vulgaris, seborrhea, female hirsutism, male pattern baldness, benign prostate hypertrophy or prostatic adenocarcinoma or compounds known to have utility when used in combination with 5-α-reductase inhibitors. Preferably, if the administration is not simultaneous, the compounds are administered in a dose time proximity to each other. Furthermore, it does not matter if the compounds are administered in the same dosage form, e.g. one compound may be administered topically and another compound may be administered orally.

Formula (II) compounds are prepared as shown in Schemes I, II and III wherein A is as described in Formula (II). As used herein $R^8$ is R or moieties which can be converted to those of R by chemical reactions readily is known to those of skill in the art, such as described in Derek Barton and U. D. Oilis, *Comprehensive Organic Chemistry: The Synthesis and Reactions of Organic Compounds*. Pub: Pergamon Press (1979), provided that $R^8$ does not include any such moieties that render inoperative the Schemes I, II or III processes. As demonstrated in the following Examples, reactions to convert $R^8$ to R are performed on products of the synthetic pathways of Schemes I, II or III or where appropriate or preferable, on certain intermediates in these synthetic pathways. For example, methylthio substituents can be converted to the methylsulfonyl by oxidation. Methoxy substituents can be converted to the hydroxy by treatment with boron tribromide. Hydroxy substituents can be converted to the carboxy by reaction with a trihaloalkylsulfonic anhydride, such as trifluoromethanesulfonic anhydride, followed by a metal catalyzed coupling reaction.

The novel compounds of Formula (II) of the present invention can be prepared by methods outlined in schemes 1-3 below and in the examples from the known and readily available steroid acid of the structure (X):

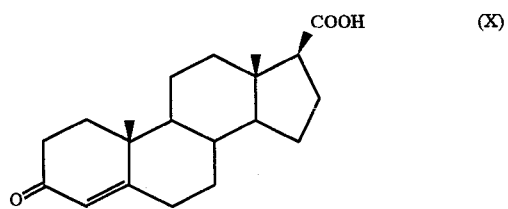

or from the known steroid acid

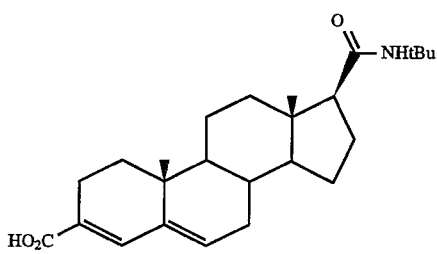

which is prepared as described in U.S. Pat. No. 5,017,568.

Scheme I

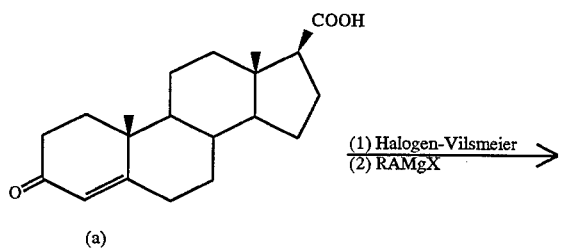
(a)

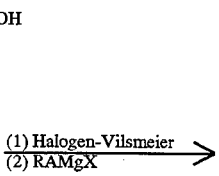

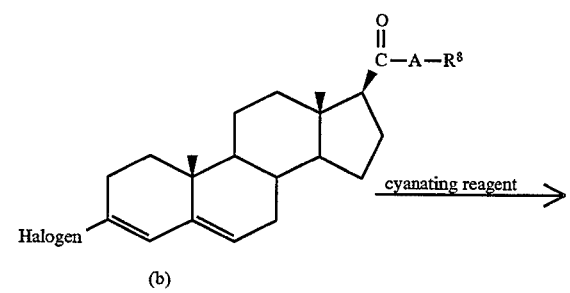
(b)

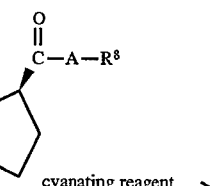

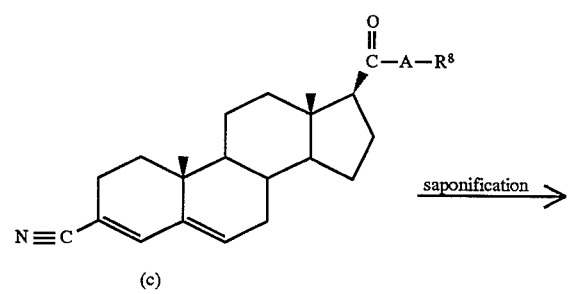
(c)

-continued
Scheme I

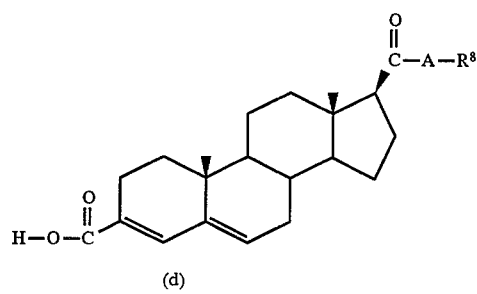
(d)

Scheme I outlines formation of Formula II compounds. As used in scheme I compound (b) is prepared from compound (a) by treating (a) with halogen-Vilsmeier reagent, described hereinbelow, in an appropriate solvent, preferably methylene chloride followed by quenching with excess Grignard reagent, described hereinbelow. The 3-cyano derivative (c) is produced by treating (b) with a cyanating reagent, described hereinbelow, in an appropriate solvent, preferably dimethylformamide. The 17-acyl derivative (c) is saponified, described hereinbelow, to yield compounds (d).

Scheme II

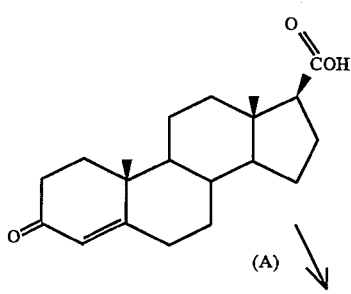
(A)

-continued
Scheme II

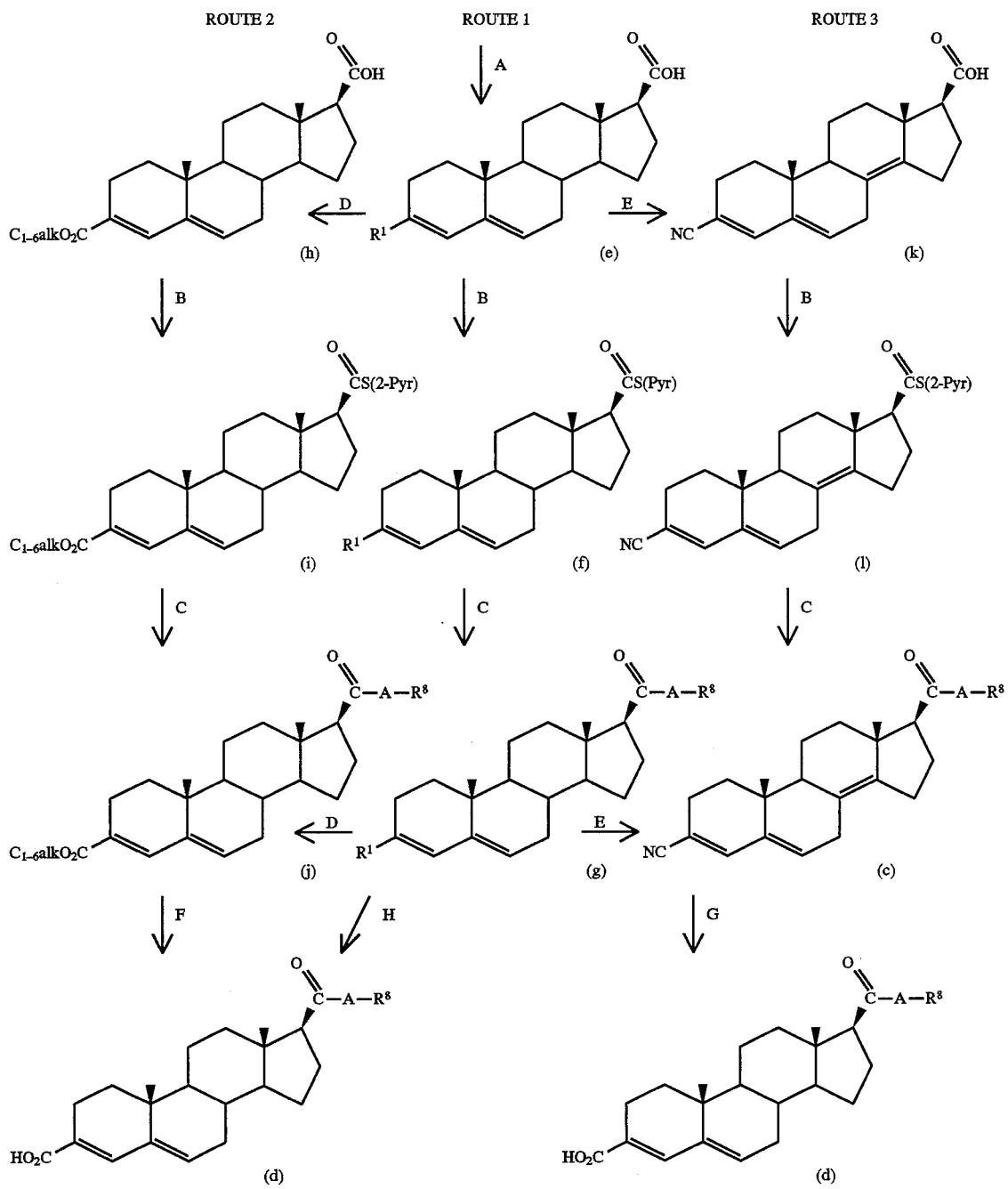

Scheme II outlines formation of Formula II compounds. As used in Scheme II A and $R^8$ are as described in Formula IV, $R^1$ is $CF_3O_2SO-$ or $FO_2SO-$. As used in scheme II in the alkylation process (step C), the pyridylthio ester is reacted with an Li-AR$^8$ or an XMgAR$^8$ (X=Cl, Br) Grignard reagent (as described hereinbelow), preferably phenylpropylmagnesium bromide, benzylmagnesium chloride, cyclohexylethylmagnesium bromide, 4-fluorophenethylmagnesium bromide, phenethylmagnesium bromide, 2,2-dimethylphenethylmagnesium bromide, cyclohexylmethylmagnesium bromide, 4,4,4 trifluorobutylmagnesium bromide, 2-(4-methoxyphenyl)ethylmagnesium chloride or 2,6-difluorobenzylmagnesium bromide in tetrahydrofuran to form the desired product, preferably 17β-(phenylpropylcarbonyl)-androsta-3,5-diene-3-carboxylic acid, 17β-(benzylcarbonyl)-androsta-3,5-diene-3-carboxylic acid, 17β-(cyclohexylethylcarbonyl)-androsta-3, 5-diene-3-carboxylic acid, 17β-(4-fluorophenethylcarbonyl)-androsta-3,5-diene-3-carboxylic acid, 17β-(phenethylcarbonyl)-androsta-3,5-diene-3-carboxylic acid, 17β-(3-methyl-3-phenyl-1-oxobutyl)-androsta-3,5-diene-3-carboxylic acid, 17β-(2-cyclohexyl-1-oxoethyl)-androsta-3, 5-diene-3-carboxylic acid, 17β-(5,5,5-trifluoro-1-oxopentyl)-androsta-3,5-diene-3-carboxylic acid, 17β-(3-(4-methoxy phenyl )-1-oxopropyl)-androsta-3,5-diene-3-carboxylic acid and 17β-(2,6-difluorobenzylcarbonyl)-androsta-3,5-diene-3-carboxylic acid respectively, in one or two steps.

In Route 1, the enone acid (a) is converted to the 3-trifluoromethylsulfonylate or 3-fluorosulfonylate derivative (e) (step A) by treating (a) with trifluoromethylsulfonyl anhydride or fluorosulfonic anhydride and an amine base, such as pyridine, preferably 2,5 di-t-butyl-3-methyl-pyridine, in an appropriate organic solvent, preferably dichloromethane at about −20° C. to 20° C., preferably 0°.

The activated ester (f) is produced (step B) by treating (e) with 2,2-dithiopyridyl and triphenylphosphine in an appropriate organic solvent solution preferably, tetrahydrofuran/ toluene at room temperature for about 8–14 hours.

The 17-acyl derivative (g) is produced (step C) by treating (f) with a Grignard reagent, described hereinbelow, in tetrahydrofuran or diethyl ether solvent, at a temperature of about −50° to −70°, for 1–16 hours.

The 3-alkyl ester (j) is produced (step D) by treating (g) under carbonylation conditions, preferably by bubbling carbon monoxide gas through a solution of (g) in an appropriate organic solvent, preferably methanol, containing palladium acetate catalyst, triphenylphosphine, and a tertiary organic amine preferably triethylamine at about room temperature for 1–16 hours. Compound (j) next is reacted with a suitable base, preferably potassium carbonate and acidified (step F) to yield compounds (d).

Compounds (d) can also be produced (step H) by treating (g) under carboxylation conditions, preferably by bubbling carbon monoxide gas through a solution of (g) in appropriate non-alcoholic solvent, preferably DMF, containing a palladium catalyst, preferably bis(triphenylphoshine)palladium II diacetate, and a carboxylate salt, preferably potassium acetate, preferably at increased temperatures.

Note that, if $R^8$ is aroyl, which also contains a protected hydroxy group, e.g. with dimethyl-t-butyl-silyl, this may be removed by treating with tetrabutylammonium floride in an appropriate, organic solvent, preferably tetrahydrofuran with a small amount of added acetic acid, from 0° C. to reflux for 1–4 hours prior to carrying out step F.

Route 2 involves converting the starting steroidal acid (a) to the 3-trifluoromethylsulfonylate or the 3-fluorosulfonylate derivative (e) by the above-described step A; carbonylating (e) to (h) by step D; forming the activated 2-pyridylthio ester (i) by step B; forming the 17-acyl compound (j) by step C; and hydrolyzing the 3-ester to the 3 add final product (d) by step F.

Route 3 involves converting the starting steroid add (a) to the 3-trifuromethylsulfonylate or the 3-fluorosulfonylate derivative (e) by the above-described step A. The 3-cyano derivative (k) is produced (step E) by treating (e) with a cyanating agent (as described hereinbelow) in an appropriate solvent, preferably dimethylformamide. The activated 2-pyridylthio derivative (l) is prepared from (k) by step B. Forming the 17-acyl compound (c) involves reacting (l) by step C. The 17-acyl derivative (c) is saponified (step G) (as described herein) to yield compounds (d).

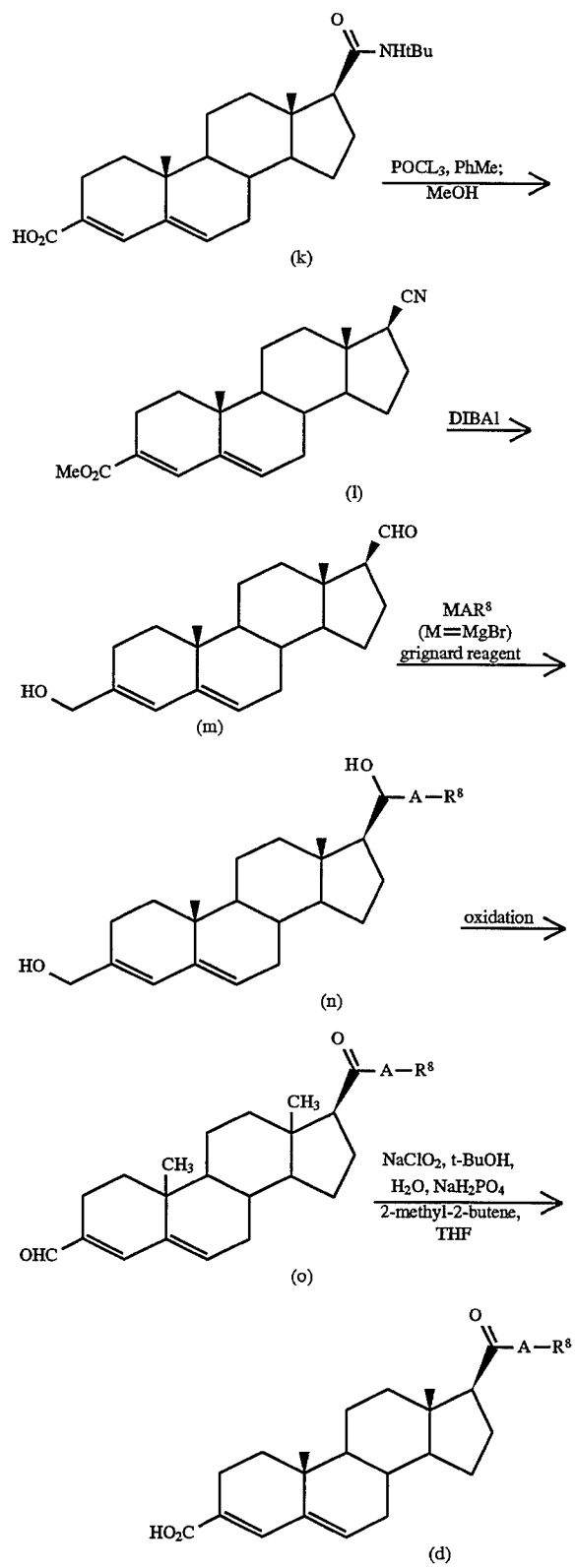

Scheme III outlines formation of Formula II compounds.
As used in Scheme III, compound (1) is prepared from compound (k) by treatment with phosphorusoxychloride in toluene followed by treatment with methanol.

Formula (l) compounds are reacted with a reducing agent, preferably diisobutylaluminum hydride, to yield formula (m) compounds.

Formula (n) compounds are produced by treating formula (m) compounds with a Grignard Reagent (as described in Scheme II) in tetrahydrofuran or diethylether solvent, at a temperature of about −50° C. to −70° C., for 1–16 hours.

Formula (o) compounds are prepared by oxidation of formula (n) compounds. Preferably said oxidation will utilize tetrapropylammonium perruthenate or a Jone's reagent.

Formula (d) compounds are prepared by oxidation of formula (o) compounds. Preferably said oxidation will utilize sodium chlorite.

As used herein Grignard reagents of the type, $XMgAR^8$, for all of the species included within the scope of this invention, are available or can be made readily by one skilled in the art.

For example, where a $AR^8$ is hydroxyphenyl, this can be derived by starting with an appropriate bromophenol, e.g. p-bromophenol, protecting the phenolic-OH with a conventional blocking group, e.g. triorganosilyl, i.e. t-butyldimethylsilyl, carrying out the Grignard reaction and then deblocking the silyl group by the use of, e.g. refluxing aqueous tetrabutylammmonium fluoride.

For a $AR^8$ being hydroxyethylphenyl, the same blocking procedure can be analogously conducted starting with the appropriate hydroxyalkyl bromophenol, e.g. p-hydroxymethylbromobenzene, or p-hydroxymethylbromobenzene, or p-hydroxyethylbromobenzene.

Where a $AR^8$ is carboxyphenyl, this can be obtained by the chromic acid oxidation of the appropriate hydroxymethylbenzene, e.g. p-bromo-hydroxymethylbenzene, formed as described above.

Where a $AR^8$ is -alkyl, the appropriate bromo-Oalkyl benzene, e.g. p-methoxybromobenzene, is utilized for the Grignard reaction.

Other halo substituted benzenes to form the appropriate Grignard reagent useful in the instant invention will be obvious to one skilled in the art from this disclosures.

Formula I compounds in which Z is in the α position are prepared from compounds which contain the corresponding β substituent by the General Method below.

General Method A

To a stinted solution of a substituted 17 β steroidal 5α-reductase inhibiting compound of Formula (II) in an appropriate solvent, preferably ethylene glycol or dimethyl sulfoxide, is added a base such as a hydroxide or alkoxide base, preferably sodium hydroxide, potassium hydroxide or sodium methoxide, at a temperature over 100° C. preferably at reflux temperatures to yield the corresponding α epimer, after isolation and work up.

In determining the appropriate solvent for conducting the epimerization, dimethyl sulfoxide or other non-reactive high boiling solvents are preferred when the starting 17β 5α-reductase inhibiting steroidal compound contains reactive substituents or reactive unsaturated bonds that are, for example, subject to nucleophilic attack and ethylene glycol, or other reactive high boiling solvents can be used when the reactivity of the substituents or any unsaturated bonds of the starting 17β 5α-reductase inhibiting steroidal compound is not a consideration.

Also within the scope of the present invention are the ketone reduction products of Formula (I) compounds, the secondary alcohols of the formula:

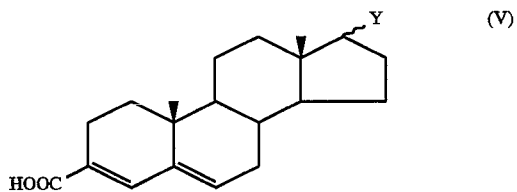

wherein

Y is α or β

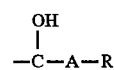

a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, $-C(O)OR^6$ and $-S(O)_nR^5$, where $R^6$ is hydrogen or alkyl, n is 0–2 and $R^5$ is hydrogen, cycloalkyl, $C_6-C_{12}$aryl, substituted cycloalkyl, substituted $C_6-C_{12}$aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, $-C(O)OR^6$, $-S(O)_nR^7$, nitro, cyano, halogen, $C_6-C_{12}$aryl, substituted $C_6-C_{12}$aryl and protected —OH, where $R^6$ is hydrogen or alkyl, n is 0–2 and $R^7$ is hydrogen or alkyl;

b) cycloalkyl is nonaromatic, unsaturated or saturated, cyclic or polycyclic $C_3-C_{12}$, optionally containing one or more heteroatoms, and optionally substituted with one or more substituents selected from the group consisting of: aryloxy, aryl, alkyl, alkoxy, acyloxy, cycloalkyl, substituted cycloalkyl, amino, N-acylamino, nitro, Cyano, oxo, hydroxy, halogen, $-C(O)OR^6$, $-S(O)_nR^5$, protected —OH and alkyl substituted with one or more substituents selected from the group consisting of: alkoxy, acyloxy, $C_6-C_{12}$aryl, substituted $C_6-C_{12}$aryl, amino, N-acylamino, oxo, hydroxy, cycloalkyl, substituted cycloalkyl, $-C(O)OR^6$, $-S(O)_nR^7$, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, $C_6-C_{12}$aryl, substituted cycloalkyl, substituted $C_6-C_{12}$aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, $-C(O)OR^6$, $-S(O)_nR^7$, nitro, cyano, halogen, $C_6-C_{12}$aryl, substituted $C_6-C_{12}$aryl and protected —OH, where $R^6$ is hydrogen or al alkyl, n is 0–2 and $R^7$ is hydrogen or alkyl; and c) aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^6$, —S(O)$_n$R$^5$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted aryloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, $C_6$–$C_{12}$aryl, substituted $C_6$–$C_{12}$aryl and protected —OH, where R$^6$ is hydrogen or alkyl, n is 0–2 and R$^7$ is hydrogen or alkyl; and pharmaceutically acceptable salts, hydrates solvates and esters thereof.

Preferred among the presently invented ketone reduction products described above are those in which A is a linear or branched, saturated or unsaturated hydrocarbon chain containing from 2–12 carbon atoms.

Particularly preferred among the presently invented ketone reduction products described above are the secondary alcohols wherein the 17

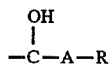

substituent is attached in the β position.

These compounds can be made by conventional sodium borohydride reduction of the carbonyl attached to A without epimerization or reducing the carboxyl in Ring A or the 3,5-double bonds. If the R substituent contains a carbonyl function, it can be selectively blocked and then regenerated after the borohydride reduction by conventional methods.

The borohydride reduction can be carried out in e.g. water or aqueous methanol, at a temperature of room temperature to 50° C. and the product then isolated and purified by conventional means. The compounds are also active as 5-alpha reductase inhibitors.

By the term "halogen-Vilsmeier reagent" as used herein is meant a halogenated disubstituted formamide reagent of the structure:

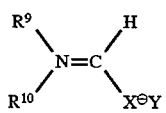

wherein R$^9$ and R$^{10}$ are independently selected from an alkyl, aryl or arylalkyl group; and X is Br or I; and y is a counter ion, which is prepared by a) reacting, preferably at reduced temperatures, a chloride source such as oxalyl chloride or thionyl chloride, with a disubstituted formamide reagent, such as a dialkyl substituted formamide reagent preferably dimethylformamide, in an appropriate solvent, preferably methylene chloride, to form a chloro-Vilsmeier reagent, said chloro-Vilsmeier reagent being reacted in situ, preferably at reduced temperatures, with a bromide source or an iodine source, preferably hydrogen bromide gas or b) reacting, preferably at reduced temperatures, a bromide source or an iodide source, preferably oxalyl bromide, with a disubstituted formamide reagent, such as a dialkyl substituted formamide reagent preferably dimethylformamide in an appropriate solvent, preferably methylene chloride.

By the term "reduced temperature" as used herein is meant below 25° C., preferably between −15° and 15° C., most preferably between 0° and 10° C.

By the term "cyanating reagent" as used herein and in the claims is meant a compound or reagents which are capable of reacting with a halogenated moiety to form a cyanated moiety under appropriate conditions.

Preferably said cyanated moiety is prepared by reacting the corresponding halogenated moiety with a cyanating agent in an appropriate solvent, such as N,N-dimethyl-N,N-propylene urea (DMPU), N,N-dimethylformamide (DMF) or N-methyl-2-pyrrolidinone (NMP), preferably DMF, at increased temperatures.

By the term "saponifying" and derivatives thereof as used herein and in the claims is meant a compound or reagent or a series of reagents which are capable of reacting with a nitrile to form a carboxylic acid substituted moiety under appropriate conditions. Preferably said carboxylic acid substituted moiety is prepared by reacting the corresponding cyanated moiety with a hydroxide base, preferably aqueous sodium hydroxide, in an appropriate solvent, such as; ethylene glycol, isopropyl alcohol or ethanol, preferably ethanol, at increased temperatures with subsequent acidification.

By the term "increased temperatures" as used herein and in the claims is meant above 25° C., preferably at reflux temperatures.

Preferably cyanating reagents for use in the presently disclosed processes utilize cyanide complexes such as described in Richard C. Larock, *Comprehensive Organic Transformations: A Guide to Functional Group Preparations*. Pub: VCH Publishers, Inc. (1989) P. 861. An example of a cyanide complex as used herein is the in situ comixture of KCN, NiBr$_2$(PPh$_3$)$_2$, Zn, PPh$_3$. Other examples include: CoCu(CN)$^{3-}$$_4$; K$_4$Ni$_2$(CH)$_6$, KCN; KCN, cat Pd(PPh$_3$)$_4$; Co(CN)$^{3-}$$_5$; CuCN and NaCu(CN)$_2$. As used herein the term "NaCu(CN)$_2$" refers to the reagent formed by co-mixing CuCN and NaCN in situ.

Preferred among the above cyanating complexes are CuCN and NaCu(CN)$_2$.

Particularly preferred among the above cyanating complexes is NaCu(CN)$_2$.

Preferably said NaCu(CN)$_2$ complex is prepared by adding 1 molar equivalent of sodium cyanide to cuprous cyanide in situ.

By the term "solvent" or "appropriate solvent" as used herein and the in the claims is meant a solvent such as methylene chloride, ethylene chloride, chloroform, ethylene glycol, carbon tetrachloride, tetrahydrofuran (THF), ethyl ether, toluene, ethyl acetate, hexane, dimethylsulfoxide (DMSO), N,N'-dimethyl-N,N'-propylene urea, N-methyl-2- pyrrolidinone, methanol, isopropylalcohol, dimethylformamide (DMF), water, pyridine, quinoline or ethanol.

Pharmaceutically acceptable salts, hydrates and solvates of Formula (I) and Formula (V) compounds are formed, where appropriate, by methods well known to those of skill in the art.

In preparing the presently invented compounds of Formula (I), novel intermediates of the following Formula (III) are synthesized;

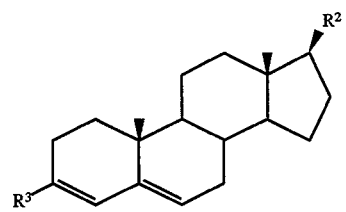

in which $R^2$ is 2-thiopyridylcarbonyl and $R^3$ is fluorosulfonyloxy or cyano.

Also, prepared in synthesizing the presently invented Formula (I) compounds were novel intermediates of the Formula (IV):

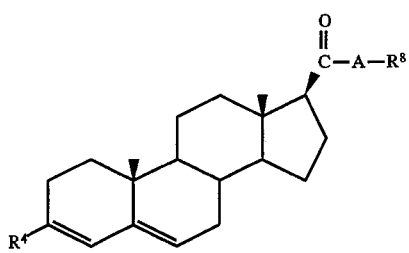

in which A is as defined in Formula (II) and $R^8$ is R as defined in Formula (II) or moieties which can be convened to those of R by known reactions such as desired in Derek Barton and U.S. Ollis, *Comprehensive Organic Chemicsty: The Synthesis and Reactions of Organic Compounds*. Pub: Pergamon Press (1979), and $R^4$ is fluorosulfonyloxy, halogen, cyano, or —CHO.

Also prepared in synthesing the presently invented Formula I compounds were novel intermediates of the structure

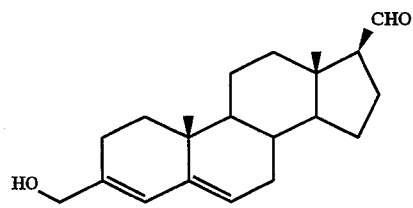

Also prepared in synthesing the presently invented Formula I compounds were novel intermediates of the Formula (VII)

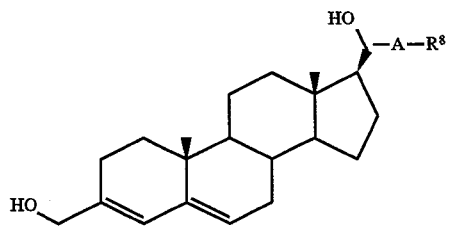

in which A and $R^8$ are as defined in Formula (IV).

A preferred process for preparing a compound of Formula (II)

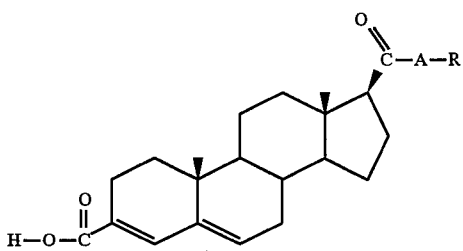

in which A is a linear or branched, saturated or unsaturated hydrocarbon containing from 1–12 carbon atoms; and R is as defined in Formula (II) above and pharmaceutically acceptable salts, hydrates, solvates and esters thereof comprises reacting a compound of the formula

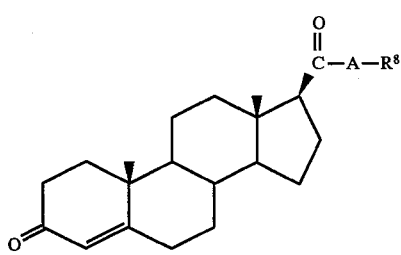

in which A and $R^8$ are as defined in Formula (IV) with fluorosulfonic anhydride and a base, preferably, 2,5-t-butyl-3-methyl-pyridine, in a solvent, preferably dichloromethane, to form a compound of the formula

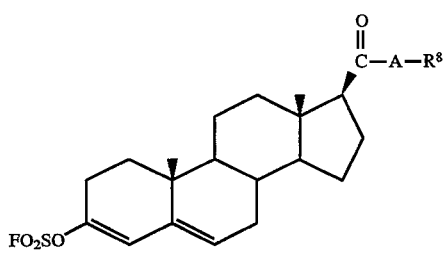

in which A and $R^8$ are as described above and subsequently reacting said compound in a metal-catalyzed coupling reaction in the presence of an appropriate coupling reagent, preferably, carbon monoxide followed by an optional, if applicable, hydrolysis reaction and optionally, if applicable converting $R^8$ to R, to form a compound of Formula II, and thereafter optionally forming a pharmaceutically acceptable salt, hydrate or solvate thereof.

The above formula (VIII) compounds are prepared by first activating the 17-position carboxylic acid substituent of compounds of structure (X), as described herein, preferably with an acid chloride, such as thionylchloride or by forming a thiopyridylester by reaction with 2,2-dithiopyridyl, and then treating with a Grignard reagent as described herein.

A preferred process for preparing a compound of Formula II

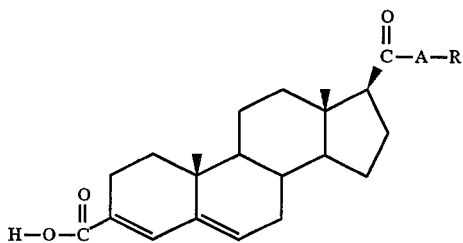

in which A and R are a defined above and pharmaceutically acceptable salts, hydrates, solvates and esters thereof comprises reacting, at a reduced temperature, a compound of the formula

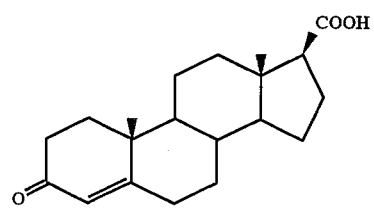

in the presence of a halogen-Vilsmeier reagent and a solvent then quenching with Grignard reagent to form a compound of the formula

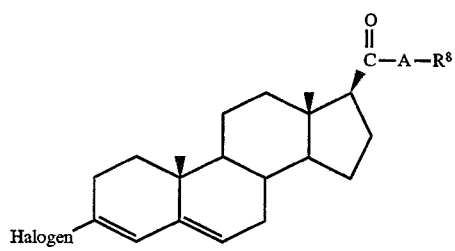

in which A and $R^8$ are as described in Formula (IV) and subsequently, in an appropriate solvent, reacting said compound with a cyanating reagent to form a compound of the formula

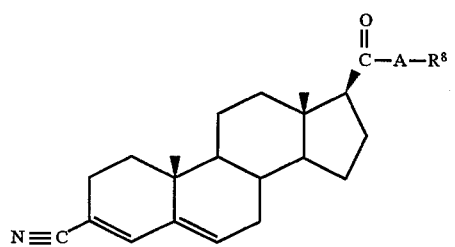

in which A and $R^8$ are as defined above and subsequently saponifying said compound and optionally, if applicable, converting $R^8$ to R, to form a compound of Formula II and thereafter optionally forming a pharmaceutically acceptable salt, hydrate or solvate.

A process for the preparation of a compound of the Formula

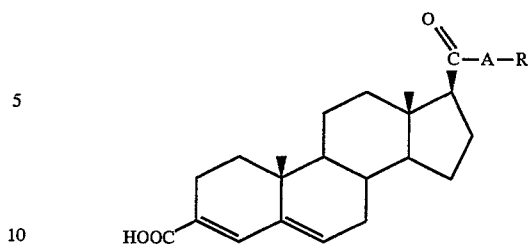

in which A and R are as defined in Formula (II); and pharmaceutically acceptable salts, hydrates, solvates and esters thereof which comprises either i) oxidation of a compound of the Formula (VII)

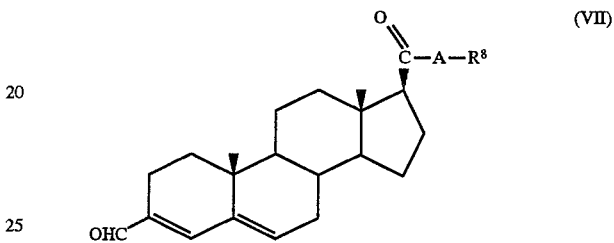

in which A and $R^8$ are as defined in Formula (IV) or (ii) reacting a compound of the Formula (XI)

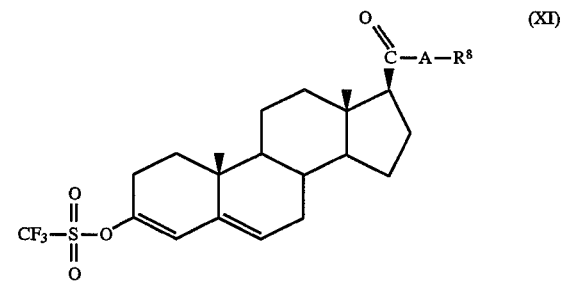

in which A and $R^8$ are as described above, in a metal-catalyzed coupling reaction in the presence of an appropriate coupling reagent, preferably, carbon monoxide followed by an optional, if applicable, hydrolysis reaction or (iii) hydrolyzing a compound of the Formula (XII)

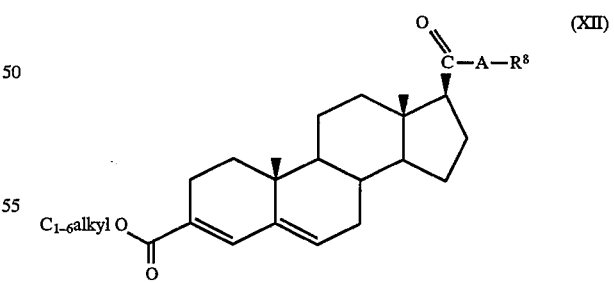

in which A and $R^8$ are as described above, and optionally, if applicable, converting $R^8$ to R and thereafter optionally forming a pharmaceutically acceptable salt, hydrate or solvate thereof.

Because the presently invented pharmaceutically active compounds inhibit steroid 5-α-reductase activity, they have therapeutic utility in treating diseases and conditions wherein decreases in DHT activity produces the desired therapeutic effect. Such diseases and conditions include acne vulgaris, seborrhea, female hirsutism, male pattern baldness, prostate diseases such as benign prostatic hypertrophy, and prostatic adenocarcinoma.

In determining potency in inhibiting the human 5α-reductase enzyme, the following procedure was employed:
Preparation of membrane particulates used as source for recombinant steroid 5α-reductase isozyme 1.

Chinese hamster ovary (CHO) cells containing expressed, recombinant human steroid 5α-reductase isoenzyme 1 (Andersson, S., Bennan, D. M., Jenkins, E. P., and Russell, D. W. (1991) Nature 354 159–161) were homogenized in 20 mM potassium phosphate, pH 6.5, buffer containing 0.33M sucrose, 1 mM dithiothreitol, and 50 μM NADPH (buffer A) using a Dounce glass-to-glass hand homogenizer (Kontes Glass Co., Vineland, N.J.). Membrane particulates were isolated by centrifugation (100,000× g at 4° C. for 60 minutes) and resuspended in 20 mM potassium phosphate, pH 6.5, containing 20% glycerol, 1 mM dithiothreitol, and 50 μM NADPH (buffer B). The suspended particulate solution was stored at −80° C.
Preparation of prostatic membrane particulates used as source for steroid 5α-reductase isozyme 2.

Frozen human prostates were thawed and minced into small pieces (Brinkmann Polytron (Sybron Corp., Westbury, N.Y.). The solution was sonicated for 3 to 5 minutes with a Sonifier (Branson Sonic Power Co.) followed by hand homogenization in a Dounce hand homogenizer. Prostatic particles were obtained by differential centrifugation at 600 or 1000× g for 20 minutes and 140,000×g for 60 minutes at 4° C. The pellet obtained from the 140,000×g centrifugation was washed with 5 to 10 tissue volumes of the buffer described above and centrifuged at 140,000×g. The resulting pellet was suspended in buffer B and the particulate suspension was stored at −80° C.
Preparation of membrane particulates used as source for recombinant steroid 5-α-reductase isozyme 2.

Chinese hamster ovary (CHO) cells containing expressed, recombinant human steroid 5-α-reductase isozyme 2 were homogenized in 20 mM potassium phosphate, pH 6.5, buffer containing 0.33M sucrose, 1 mM dithiothreitol, and 50 μM NADPH (buffer A) using a Douce hand homogenizer. Membrane particulates containing the recombinant human enzyme were isolated by centrifugation (100,000× g at 4° C. for 60 minutes) and resuspended in 20 mM potassium phosphate, pH 6.5 containing 20% glycerol, 1 mM dithiothreitol, and 50 μM NADPH (buffer B). The suspended particulate solution was stored at −80° C. until used.
Assay for enzymes activities and inhibitors potency.

A constant amount of [$^{14}$C]testosterone (50 to 55 mCi/mmol) in ethanol and varying mounts of potential inhibitor in ethanol were deposited in test tubes and concentrated to dryness in vacuo. To each tube was added buffer, 10 μL (recombinant isoenzyme 1 or isoenzyme 2) or 20 μL (isoenzyme 2 from human prostate tissue) of 10 mM NADPH and an aliquot of asteroid 5α-reductase preparation to a final volume of 0.5 mL. Assays for human steroid 5α-reductase isoenzyme 1 were conducted with a sample of the recombinant protein expressed in CHO cells in 50 mM phosphate buffer, pH 7.5 while assays of isoenzyme 2 were conducted with a suspension of human prostatic particulates and/or recombinant protein expressed in CHO cells in 50 mM citrate buffer at pH 5.0.

After incubating the solution at 37° C. for 20 or 30 minutes the reaction was quenched by the addition of 4 mL, ethyl acetate and 0.25 μmol each of testosterone, 5α-dihydrotestosterone, androstanediol, and androstanedione as carriers. The organic layer was removed to a second test tube and evaporated to dryness in a Speed Vac. The residue was dissolved in 40 μL chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan Inc., Washington, D.C.). The percent of recovered radiolabel converted to product was calculated, from which enzyme activity was determined. All incubations were conducted such that no more than 20% of the substrate (testosterone) was consumed.

The experimentally obtained data was computer fit to a linear function by plotting the reciprocal of the enzyme activity (1/velocity) against the variable inhibitor concentration; apparent inhibition constants ($K_{i,app}$) were determined by the Dixon analysis (Dixon, M. (1953).

The value for the inhibition constant (Ki) was calculated from known procedures (Levy, M. (1989), Biochemistry, 29:2815–2824).

The pharmaceutically active compounds within the scope of this invention are useful in inhibiting steroid 5-α-reductase in a mammal, including humans, in need thereof.

Compounds within the scope of this invention have been tested and have shown an activity of from 85 Ki(nM) to 2 Ki(nM) against isozyme 1 and an activity of from 7 Ki(nM) to 0.2 Ki(nM) against isozyme 2. Particularly preferred among the compounds of the invention and the compounds used in the invented pharmaceutical compositions and invented methods are 17β-(phenylpropylcarbonyl)-androsta-3,5-diene-3-carboxylic acid, 17β-(benzylcarbonyl)-androsta-3,5-diene-3-carboxylic acid, 17β-(cyclohexylethylcarbonyl)-androsta-3,5-diene-3-carboxylic acid, 17β-(5,5,5-trifluoro-1-oxopentyl)-androsta-3,5-diene-3-carboxylic acid, 17β-(2-cyclohexyl-1-oxoethyl)-androsta-3,5-diene-3-carboxylic acid, 17β-(3-methyl-3-phenyl-1-oxobutyl)-androsta-3,5-diene-3-carboxylic acid, 17β-(phenethylcarbonyl)-androst-3,5-diene-3-carboxylic acid, 17β-(3-(4-methoxy phenyl)-1-oxopropyl)-androsta-3,5-diene-3-carboxylic acid, 17β-(3-(4-hydroxy phenyl)-1-oxopropyl)-androsta-3,5-diene-3-carboxylic acid, 17β-(4-fluorophenethylcarbonyl)-androsta-3,5-diene-3-carboyxlic acid and 17β-(2,6-difluorobenzylcarbonyl)-androsta-3,5-diene-3-carboxylic acid.

The pharmaceutically active compounds of the present invention are incorporated into convenient dosage forms such as capsules, tablets, or injectable preparations. Solid or liquid pharmaceutical careers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.01–1000 mg/kg of active compound, preferably 0.1–100 mg/kg. When treating a human patient in need of steroid 5-α-reductase inhibition, the selected dose is administered preferably from 1–6 times daily, orally or parenterally. Preferred fores of parenteral administration include topically, rectally, transdermally, by injection and continuously by infusion. Oral dosage units for human administration preferably contain from 0.1 to 500 mg of active compound. Oral administration, which uses lower dosages is preferred. Parenteral administration, at high dosages, however, also can be used when safe and convenient for the patient.

The method of this invention of inhibiting steroid 5-α-reductase activity in mammals, including humans, comprises administering to a subject in need of such inhibition an effective steroid 5-α-reductase inhibiting amount of a pharmaceutically active compound of the present invention.

The invention also provides for the use of a compound of Formula (I) or a compound of Formula (V) in the manufacture of a medicament for use in the inhibition of steroid 5-α-reductase.

The invention also provides for a pharmaceutical composition for use in the treatment of benign prostate hypertrophy which comprises a compound of Formula I or a compound of Formula (V) and a pharmaceutically acceptable carrier.

The invention also provides for a pharmaceutical composition for use in the treatment of prostatic adenocarcinoma which comprises a compound of Formula I or a compound of Formula (V) and a pharmaceutically acceptable carrier.

The invention also provides for a process for preparing a pharmaceutical composition containing a pharmaceutically acceptable carrier or diluent and a compound of Formula I or a compound of Formula (V) which comprises bringing the compound of Formula I or the compound of Formula CV) into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to treat the disease states of ache vulgaris, seborrhea, female hirsutism, male pattern baldness, benign prostate hypertrophy or prostatic adenocarcinoma or compounds known to have utility when used in combination with 5-α-reductase inhibitors. Particularly preferred is the co-administration of a 5-α-reductase inhibitor, as disclosed herein, and minoxidil for use in the treatment of male pattern baldness. Particularly preferred is the co-administration of a 5α-reductase inhibitor, as disclosed herein, and a α-receptor antagonist for use in the treatment of benign prostatic hypertrophy. Preferred is the co-administration of a 5-α-reductase inhibitor, as disclosed herein, and an aromatase inhibitor for use in the treatment of benign prostatic hypertrophy. Preferred is the co-administration of a 5-α-reductase inhibitor, as disclosed herein, a α-receptor antagonist and an aromatase inhibitor for use in the treatment of benign prostatic hypertrophy.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1

Corresponding to Scheme I

17β-(Phenethylcarbonyl)-androsta-3,5-diene-3-carboxylic acid (i). 17β-(Phenethylcarbonyl)-androsta-3-bromo-3,5-diene A flask under nitrogen atmosphere is charged with 100 mL of methylene chloride and 6.12 mL (2.5 molar equivalents) of dimethylformamide. The solution is cooled to 0°–5° C., and treated with 6.9 mL (2.5 molar equivalents) of oxalyl chloride while maintaining the temperature between 0°–10° C. A white precipitate formed. After stirring for one hour, 50.1 grams (19.6 molar equivalents) of hydrogen bromide gas is bubbled through the solution while maintaining the temperature between 0°–10° C. The suspension becomes a clear colorless solution. The solution is degassed by reducing the solution volume by about one-half by vacuum distillation and restoring to its original volume with methylene chloride. This concentration/refill procedure is repeated. Androst-4-en-3-one-17b-carboxylic acid, 10.0 grams (1 molar equivalent), is added to the resulting white suspension and the mixture is warmed to room temperature and stirred for 2 hours. The reaction mixture is quenched into a vessel containing 100 mL of methylene chloride and 1 molar equivalent of phenethylmagnesium bromide while maintaining the temperature between 0°–10° C. The mixture is stirred for 30 minutes. About 100 mL of water is added and the biphase mixture is filtered through a pad of Celite. The organic phase is separated and reduced to about half its volume by vacuum distillation. The solution is restored to its original volume with acetone. This concentration/fill procedure is repeated twice more. The resulting acetone solution (about 300 mL) is warmed to about 50° C. and was treated with about 100 mL of water to precipitate the product. The suspension is cooled, and the product, 17β-(phenethylcarbonyl)-androsta-3-bromo-3,5-diene, is isolated by filtration and dried.

(ii) 17β-(Phenethylcarbonyl)-androsta-3-cyano-3,5-diene

A stirred mixture of 17β-(phenethylcarbonyl)-androsta-3-bromo-3,5-diene (50 grams, 1 molar equivalent), cuprous cyanide (11.0 grams, 1 molar equivalents), and dimethylformamide (200 mL,) is heated to reflux for 3.5 hours. The reaction is cooled to 90°–100° C. and quenched with stirring into a solution of 100 mL, of conc. aqueous ammonia and 200 mL of water. The reaction flask is rinsed out with 25 mL, of dimethylformamide, which is also added to the quench solution. The resulting suspension is extracted twice with 200 mL portions of methylene chloride, and the organic extracts is filtered through a pad of celite. The organic phase is washed with three 200 mL portions of 50/50 v/v conc. aqueous ammonia/water, followed by two 200 mL, portions of water. The organic phase is concentrated under vacuum to 150 mL, and 250 mL, of ethanol is added. The solution is again concentrated under vacuum to 150 mL, and 250 mL, of ethanol is added. The solution is concentrated under vacuum to 300 mL, and 30 mL, of water is added to induce crystallization. The resulting suspension is chilled for 2 hours at 0°–5° C. The solid product is collected by filtration and is dried at 65° C. under vacuum to afford 17β-(phenethylcarbonyl)-androsta-3-cyano-3,5-diene.

(iii) 17β-(phenethylcarbonyl)-androsta-3,5-diene-3-carboxylic acid

A mixture of 17β-(phenethylcarbonyl)-androsta-3-cyano-3,5-diene (20.0 grams, 1 molar equivalent), 50% aqueous sodium hydroxide (80 mL, 30 molar equivalents), and ethanol (200 mL,) is heated to reflux for 18 hours. The reaction suspension is cooled to 50° C. and is added to a stirred mixture of 6N hydrochloric acid (300 mL,) and methylene chloride (200 mL,). The final pH of the aqueous phase is 1.5–2.0. The organic phase is separated and the aqueous phase is reextracted with 250 mL of methylene chloride. The combined organic phases are stirred with 2 grams of decolorizing charcoal for one hour and are filtered through a pad of celite. The organic phase was concentrated under vacuum to 120 mL and 200 mL, of ethyl acetate is added. The suspension is again concentrated under vacuum to 120 mL, and 200 mL, of ethyl acetate is added. The resulting suspension is concentrated under vacuum to a final volume of 120 mL, and is heated at reflux for 2 hours. The suspension is chilled at 0°–5° C. for two hours and filtered. The solid product is dried under vacuum at 65° C. to afford 17β-(phenethylcarbonyl)-androsta-3,5-diene-3-carboxylic acid.

EXAMPLE 2

Corresponding to Scheme II

17β-(Phenethylcarbonyl)-androsta-3,5-diene-3-carboxylic Acid (i). 3-(trifluoromethanesulfonyl)-androst-3,5-diene-17β-carboxylic acid A solution of androst-4-en-3-one-17β-carboxylic acid (8.0 g; 25 mmol), 2,6-di-t-butyl-4-methyl pyridine (16.6 g; 62 mmol) and trifluoromethane sulfonic anhydride (11 mL; 66 mmol) in methylene chloride was stirred at 5° C. for 20 hours. The organic solvent was evaporated and the residue is dissolved in tetrahydrofuran water (99.5:0.5) with 4-dimethylaminopyridine (9.0 g) which upon acidification with hydrochloric acid followed by conventional workup yield 13 grams of the title compound (92% yield). MP 182° C.

(ii). S-(2-pyridyl)-3-(trifluoromethanesulfonyl)-androsta-3,5-diene-17β-thiocarboxylate A solution of 3-(trifluoromethanesulfonyl)-androsta-3,5-diene-17β-carboxylic acid (6.2 g; 14.9 mmol), triphenylphosphine (9.92 g; 38 mmol) and, 2,2'-dipyridyl disulfide (8.68 g; 39.5 mmol) in CH$_2$CL$_2$ (50 mL) was stirred under nitrogen for 20 hours. The reaction mixture was concentrated and the residue was passed directly through silica gel and appropriate fractions evaporated to yield 4.0 g of the title compound (50% yield). MP 120°–122° C.

(iii). 17β-(Phenethylcarbonyl)-androsta-3,5-diene-3-trifluoromethane sulfonate

To a solution of S-(2-pyridyl)-3-(trifluoromethanesulfonyl)-androsta-3,5-diene-17β-thiocarboxylate (0.3 g; 0.56 mmol) in tetrahydrofuran (20 ml) at about –50° C. was added phenethylmagnesium bromide (1.6 mmol). The reaction mixture was warmed to about –10° C., and diluted with a saturated aqueous ammonium chloride solution. Conventional workup with subsequent isolation by column chromatography yielded 166 mg of the title compound (60% yield). MP 98°–99° C.

(iv) 17β-(Phenethylcarbonyl)-androsta-3,5-diene-3-carboxylic acid

A mixture of 17β-(phenethylcarbonyl)-androsta-3,5-diene-3-trifluoromethane sulfonate (0.125 g; 0.23 mmol), potassium acetate (0.130 g; 1.32 mmol) and bis (triphenylphosphine) palladium (II) diacetate (0.015 g; 0.02 mmol) in DMF (3ml) was purged with carbon monoxide for 2 minutes and stirred under a CO ballon at 60° C. for 2 hours. Reaction was diluted with water; acidified with 0.5 NHCl and extracted with ethylacetate and ethyl acetate extracts washed with water, dried (MgSO4) and evaporated under vacuum. The residue was chromatographed on a silica gel column eluting with hexane: ethylacetate: acetic acid 70:30:1. The solid obtained was recrystallized from acetonitrile to give 17 mg (17%) of white solid. MP 218°–220° C.

EXAMPLE 3

Corresponding to Scheme II

17β-(4-Fluorophenethylcarbonyl)-androsta-3,5-diene-3-carboxylic Acid

The title compound is prepared according to Example 2 (i-iv) by substituting 4-fluorophenethylmagnesium bromide for phenethylmagnesium bromide in step iii.

EXAMPLE 4

Corresponding to Scheme II

17β-(Phenylpropylcarbonyl)-androsta-3,5-diene-3-carboxylic Acid

The title compound was prepared according to Example 2 (i-iv) by substituting phenylpropylmagnesium bromide for phenethylmagnesium bromide in step iii. MP 208°–210° C.

EXAMPLE 5

Corresponding to Scheme II

17β-(Benzylcarbonyl)-androsta-3,5-diene-3-carboxylic Acid

The title compound was prepared according to Example 2 (i-iv) by substituting benzylmagnesium chloride for phenethylmagnesium bromide in step iii. MP 258° C.

EXAMPLE 6

Corresponding to Scheme II

17β-(Cyclohexylethylcarbonyl)-androsta-3,5-diene-3-carboxylic Acid

The title compound was prepared according to Example 2 (i-iv) by substituting cyclohexylethylmagnesium bromide for phenethylmagnesium bromide in step iii. MP 247° C.

EXAMPLE 7

Corresponding to Scheme III

17β-(2,6-difluorobenzylcarbonyl)-androsta-3,5-diene-3-carboxylic acid

The title compound is prepared according to Example 10 (i-v) by substituting 2,6-difluorobenzylmagnesium bromide for 4,4,4-trifluorobutylmagnesium bromide in step iii.

EXAMPLE 8

Corresponding to Scheme II

17β-(phenethylcarbonyl)-androsta-3,5-diene-3-carboxylic Acid (i). 3-(fluorosulfonyloxy)-androsta-3,5-diene-17β-carboxylic acid A solution of androsta-4-en-3-one-17β-carboxylic acid, 2,6-di-t-butyl-4-methyl pyridine and fluorosulfonic anhydride in methylene chloride is stirred at 5° C. for 20 hours. The reaction mixture is washed with aqueous hydrochloric acid and water. The organic phase is concentrated and the resulting residue is purified by column chromatography to yield the title compound.

(ii). S-(2-pyridyl)-3-(fluorosulfonyloxy)-androsta-3,5-diene-17β-thiocarboxylate A solution of 3-(fluorosulfonyloxy)-androsta-3,5-diene-17β-carboxylic acid, triphenylphosphine and, 2,2'-dipyridyl disulfide in toluene is stirred under nitrogen for 20 hours. The reaction mixture is concentrated and the residue is passed directly through silica gel and appropriate fractions evaporated to yield title compound.

(iii). 17β-(Phenethylcarbonyl)-androsta-3,5-diene-3-fluorosulfonate

To a solution of S-(2-pyridyl)-3-(fluorosulfonyloxy)-androsta-3,5-diene-17β-thiocarboxylate in tetrahydrofuran at about −50° C. is added phenethylmagnesium bromide. The reaction mixture is warmed to about −10° C. and diluted with a saturated aqueous ammonium chloride solution. Conventional workup with subsequent isolation by column chromatography yields title compound.

(iv). Methyl 17β-(phenethylcarbonyl)-androsta-3,5-diene-3-carboxylate

A solution of 17β-(phenethylcarbonyl)-androsta-3,5-diene-3-fluorosulfonate, triphenyl phosphine, palladium II acetate, triethylamine, methanol and dimethyl formamide is stirred vigorously under a carbon monoxide atmosphere for 20 hours. Conventional workup with subsequent isolation by column chromatography yields title compound.

(v). 17β-(phenethylcarbonyl)-androsta-3,5-diene-3-carboxylic acid

A mixture of methyl 17β-(phenethylcarbonyl)-androsta-3,5-diene-3-carboxylate, $K_2CO_3$, water and methanol is heated at reflux for about 5 hours. Acidification followed by conventional workup yields title compound.

EXAMPLE 9

Corresponding to Scheme II

17β-(Phenethylcarbonyl)-androsta-3,5-diene-3-carboxylic Acid (i). 3-(Fluorosulfonyloxy)-androsta-3,5-diene-17β-carboxylic acid.

The title compound is prepared according to Example 8(i).

(ii). 3-Cyano-androsta-3,5-diene-17β-carboxylic acid.

A solution of 3-(fluorosulfonyloxy)-androsta-3,5-diene-17β-carboxylic acid in dimethylformamide is treated with an excess of cuprous cyanide at reflux. The reaction solution is quenched into aqueous ammonia and is filtered. The filtered solids are dissolved in methylene chloride/aqueous hydrochloric acid. Conventional workup and isolation by column chromatography yields the title compound.

(iii). S-(2-pyridyl)-3-cyano-androsta-3,5-diene-17β-thiocarboxylate.

The title compound is prepared according to Example 2(ii) by substituting 3-cyano-androsta-3,5-diene-17β-carboxylic acid, prepared as in Example 9(ii), for 3-(trifluoromethanesulfonyl)-androsta-3,5-diene-17β-carboxylic acid.

(iv). 3-cyano-17β-(Phenethylcarbonyl)-androsta-3,5-diene.

The title compound is prepared according to Example 2(iii) by substituting S-(2-pyridyl)-3-cyano-androsta-3,5-diene-17β-thiocarboxylate, as prepared in Example 9(iii), for S-(2-pyridyl)-3-(trifluoromethanesulfonyloxy)-androsta-3,5-diene-17β-thiocarboxylate.

(v). 17β-(phenethylcarbonyl)-androsta-3,5-diene-3-carboxylic acid.

A mixture of 3-cyano-17β-(phenethylcarbonyl)-androsta-3,5-diene excess sodium hydrochloride and ethanol is heated at reflux. The resulting mixture is quenched with aqueous hydrochloric acid, and is extracted with methylene chloride. Conventional workup and isolation by column chromatography yields the title compound.

EXAMPLE 10

Corresponding to Scheme III

17β-(5,5,5-trifluoro-1-oxopentyl)-androsta-3,5-diene-3-carboxylic acid i) methyl 17β-cyano-androsta-3,5-diene-3-carboxylate Phosphorus oxychloride (40ml, 429 mmol) was added to a solution of (17β)-17-N-t-butyl carboxamidyl androsta-3,5-diene-3-carboxylic acid (15.5 g, 39 mmol) in benzene (500 mL) and was heated to reflux. After 12 h the reaction was treated with MeOH (10 mL), then aqueous $NaHCO_3$, extracted with $CH_2Cl_2$, dried (MgSO4), filtered, concentrated, chromatographed (silica gel, 20% EtOAc/hexanes), and recrystallized (EtOAc/hexanes) to yield the title compound as a yellow solid.

ii) 17β-carboxaldehydo- androsta-3,5-diene-3-methanol

Diisobutyl aluminum hydride (1.0M in toluene, 60 mL, 60 mmol) was added to a solution of methyl (17β)-17-cyano androsta-3,5-diene-3-carboxylate (10 g, 29 mmol) in toluene (200 mL) at RT. After 3.5 h, the reaction was quenched with aqueous $H_2SO_4$ (700 mL) and was stirred for 2 h. The organic layer was extracted with brine, $H_2O$, then was dried (MgSO4), filtered, concentrated, and chromatographed (20% EtOAc/hexanes) to yield the title compound as a yellow solid.

iii) 17β-(5,5,5-trifluoro-1-hydroxypentyl)-androsta-3,5-diene-3-methanol 4,4,4-trifluorobutyl magnesium bromide (0.25M in THF, 4.0 ml, 1.0 mmol) was added to a solution of (17β)-17-carboxaldehydo- androsta-3,5-diene-3-methanol (50 mg, 0.16 mmol) in THF at 0 degrees C. After 0.5 h the reaction was quenched with aqueous ammonium chloride, the aqueous layer was extracted with EtOAc, the combined organic extracts were dried (MgSO$_4$), filtered, concentrated, and chromatographed (silica gel, 20% EtOAc) to yield the title compound.

iv) 17β-(5,5,5-trifluoro-1-oxopentyl)-androsta-3,5-diene-3-carboxaldehyde

Tetrapropyl ammonium perruthenate (10 mg, 0.028 mmol) was added to a solution of (17β)-17-(5,5,5-trifluoro-1-hydroxypentyl)-androsta-3,5-diene-3-methanol (65 mg, 0.15 mmol) and 4-methylmorpholine N-oxide (80 mg, 0.68 mmol) in $CH_2Cl_2$ (2.0 ml) at RT. After 1 h the reaction was flash chromatographed (silica gel, 20% EtOAc/80% hexanes) to yield the title compound.

v) 17β-(5,5,5-trifluoro-1-oxopentyl)-androsta-3,5-diene-3-carboxylic acid

Sodium chlorite (53 mg, 0.6 mmol) was added to a mixture of 17β-(5,5,5-trifluoro-1-oxopentyl)-androsta-3,5-diene-3-carboxaldehyde (50 mg, 0.12 mmol), sodium phosphate, monobasic monohydrate (140 mg, 1.18 mmol) in 2-methyl-2-butene in THF (2.0M, 3.0 ml), $H_2O$ (0.5 mL), and t-butanol (0.5 ml) at RT. After 6 h acetic acid (3.0 mL) was added, then the aqueous layer was extracted with EtOAc (10 mL), the combined organic extracts were dried (MgSO$_4$), filtered, concentrated, and flash chromatographed (silica gel, 1% AcOH/19% EtOAc/80% hexanes) to yield the title compound as a white waxy solid. ESMS m/e 439 [M+H]$^+$

EXAMPLE 11

Corresponding to Scheme III

17β-(2-cyclohexyl-1-oxoethyl)-androsta-3,5-diene-3-carboxylic acid i) 17β-(2-cyclohexyl-1-oxoethyl)-androsta-3,5-diene-3-carboxylic acid Following the procedure of Example 10 (i)–(v), except substituting cyclohexyl methyl magnesium bromide for 4,4,4-trifluorobutyl magnesium bromide in step iii, the title compound was prepared as a white solid MP 257° C. Dec. MS (DCI/NH$_3$) m/e 425 [M+H]$^+$.

EXAMPLE 12

Corresponding to Scheme III

17β-(3-methyl-3-phenyl-1-oxobutyl)-androsta-3,5-diene-3-carboxylic acid i) 17β-(3-methyl-3-phenyl-1-oxobutyl)-androsta-3,5-diene-3-carboxylic acid Following the procedure of Example 10 (i)–(v), except substituting 2-methyl, 2-phenyl propyl magnesium bromide for 4,4,4-trifluorobutyl magnesium bromide in step iii, the title compound was prepared as a white solid MP 192° C. Dec. MS (DCI/NH$_3$) m/e 461 [M+H]$^+$.

EXAMPLE 13

Corresponding to Scheme III.

17β-(3-(4-methoxy phenyl)-1-oxopropyl)-androsta-3,5-diene-3-carboxylic acid i) 17β-(3-(4-methoxy phenyl)-1-oxopropyl)-androsta-3,5-diene-3-carboxylic acid Following the procedure of Example 10(i)–(v), except substituting 2-(4-methoxy phenyl) ethyl magnesium chloride for 4,4,4-trifluorobutyl magnesium bromide in step iii, the title compound was prepared as a white solid MS(DCI/NH$_3$)m/e 463[M+H]$^+$.

EXAMPLE 14

Functional Group Interchange of Example 13

17β-(3-(4-hydroxy phenyl)-1-oxopronyl)-androsta-3,5-diene-3-carboxylic acid

Boron tribromide (0.4 mL, 0.4 mmol, 1.0M in CH$_2$Cl$_2$) was added dropwise to a solution of 17β-(3-(4-methoxy phenyl)-1-oxopropyl)-androsta- 3,5-diene-3-carboxylic acid (60 mg, 0.129 mmol) in CH$_2$Cl$_2$ (2.0 ml) at 0° C. and was stirred for 0.5 hours, then was warmed to room temperature and was stirred an additional 2.5 hours. The reaction was quenched with 0.5N HCL (5.0 ml), then was extracted with CH$_2$Cl$_2$ (2×10 mL). The combined organic extracts were dried (MgSO$_4$), filtered, concentrated in vacuo, and chromatographed (silica gel, 1% AcOH/19% EtOAc/80% hexanes) to yield the title compound as a yellow solid MS (DCI/NH$_3$) m/e 449 [M+H]$^+$.

EXAMPLE 15

Corresponding to General Method A.

17α-(phenethylcarbonyl)-androsta-3,5-diene-3-carboxylic Acid

Into a 250 mL 3-neck round bottom flask is placed 17β-(phenethylcarbonyl)-androsta-3,5-diene-3-carboxylic acid and an excess of sodium hydroxide. To the flask is added dimethyl sulfoxide as a solvent. The mixture is heated to reflux for 3 hours. Standard workup followed by isolation by preparative HPLC yields title compound.

EXAMPLE 16

17β-[(4-fluorophenyl)-1-oxonpropyl]-3,5-androstadiene-3-carboxylic acid (i) S-(2-pyridyl)-androst-4-ene-3-one-17β-thiocarboxylate A mixture of 3-oxo-4-androstene-17β-carboxylic acid (0.95 g, 3 mmol), triphenylphosphine (1.6 g, 6 mmol), 2,2'-dipyridyl disulfide (1.32 g, 6 mmol) and toluene (250 ml) was stirred under argon at room temperature overnight. The resulting homogeneous solution was concentrated in vacuo, and chromatographed (silica gel, 30% EtOAc in hexanes) to give 0.87 g (71%) of white solid.

(ii) 17β-[3-(4-fluorophenyl)-1-oxopropyl]-androst-4-ene-3-one p-fluorophenylethylmagnesium bromide (5 mmol in 10 mL THF) was added slowly to a solution of S-(2-pyridyl)-1-androst-4-ene-3-one-17β-thiocarboxylate (1.2 g. 3 mmol) in THF (30 mL) at −78° C. After 30 minutes the mixture was quenched with saturated NH$_4$Cl and extracted with EtOAc. The organic extract was washed with brine, dried (MgSO$_4$), filtered, concentrated in vacuo, and chromatographed (silica gel, 15% EtOAc in hexanes →20% EtOAc in hexanes) to give an oil, 0.78 (62%).

(iii) Trifluoromethyl-17β-[3-(4-fluorophenyl)-1-oxopropyl]-androsta-3,5-diene-3-sulfonate To a solution of 17β-[3-(4-fluorophenyl)-1-oxopropyl]-androst-4-ene-3-one (0.77 g, 1.8 mmol) and 2,6-di-tert-butyl-4-methylpyridine (0.51 g, 2.5 mmol) in CH$_2$Cl$_2$ (20 mL) was slowly added trifluoromethanesulfonic anhydride (0.75 g, 2.7 mmol). After stirring for 2 hours at room temperature, the reaction mixture was washed with dilute HCl, water, dilute NaHCO$_3$, brine, dried (MgSO$_4$), filtered, concentrated in vacuo, and chromatographed (silica gel, hexanes 5% → EtOAc in hexanes) to give 0.44 g of white solid (44% yield).

(iv) 17β-[3-(4-fluorophenyl)-1-oxopropyl]-3,5-androstadiene-3-carboxylic acid

A mixture of trifluoromethyl -17β-[3-(4-fluorophenyl)-1-oxopropyl]-androsta-3,5-diene-3-sulfonate (0.28 g, 0.5 mmol), palladium (II) acetate (5.6 mg, 0.025 mmol), triphenylphosphine (13 mg, 0.05 mmol), potassium acetate (0.19 g, 2 mmol) and DMF (6 ml) was heated at 60° C. under an atmosphere of CO for 2.5 hours. The cooled mixture was diluted with ice water, acidified with dilute HCl and extracted with CH$_2$Cl$_2$. The organic extract was washed with water, brine, dried (MgSO$_4$), filtered, concentrated in vacuo, and chromatographed (silica gel, 1% AcOH/19% EtOAc/80% hexanes) to yield the title compound 0.12 g (53%). Recrystallized from methanol-acetone. mp 220°–220° C. analysis for C$_{29}$H$_{35}$FO$_3$0.25 H$_2$O(455.1)

|   | Cal'd | Found |
|---|---|---|
| C | 76.54 | 76.61 |
| H | 7.86 | 7.88 |
| MS (DCI/NH$_3$) m/e 451 [M + H]$^+$ | | |

EXAMPLE 17

17β-[1(R)-hydroxy-3-phenylpropyl]-androsta-3,5-diene-3-carboxylic acid and 17β-[1(S)-hydroxy-3-phenylpropyl]-androsta-3,5-diene-3-carboxylic acid (i) A solution of 17β-(phenethylcarbonyl)-androsta-3,5-diene-3-carboyxlic acid (50 mg in 10 mL of MeOH and 1 mL of H₂O ) prepared according to Example 2(i–iv) is treated with 2 eq of LiBH₄. The mixture is warmed to 40° C. and stirred overnight. EtOAc is added and the mixture is filtered, dried and concentrated. Chromatography (silica gel, eluting 30% EtOAc in hexane with 0.5% HOAc) provides the title compounds of undetermined C-20 stereochemistry.
(ii) Pure (R) and (S) forms are obtained by separation techniques readily available and known to those of skill in the art.

EXAMPLE 18

An oral dosage form for administering Formula I compounds is produced by screening, mixing, and filling into hard gelatin capsules the ingredients in the proportions shown in Table 1, below.

TABLE I

| Ingredients | Amounts |
| --- | --- |
| 17β-(phenethylcarbonyl)-androsta-3,5-diene-3-carboxylic acid | 50 mg |
| magnesium stearate | 5 mg |
| lactose | 75 mg |

EXAMPLE 19

The sucrose, calcium sulfate dihydrate and Formula (I) compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 17β-(phenethylcarbonyl)-androsta-3,5-diene-3-carboxylic acid | 100 mg |
| calcium sulfate dihydrate | 150 mg |
| sucrose | 20 mg |
| starch | 10 mg |
| talc | 5 mg |
| stearic acid | 3 mg |

EXAMPLE 20

17β-(phenethylcarbonyl)-androsta-3,5-diene-3-carboxylic acid, 75 mg, is dispursed in 25 mL of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

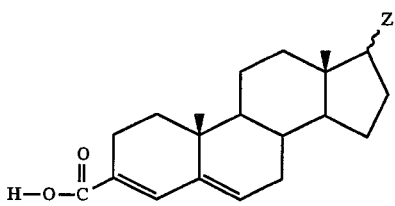

wherein

Z is α or β

$$-\overset{O}{\underset{\|}{C}}-A-R$$

in which

A is a linear or branched, saturated or unsaturated hydrocarbon chain containing from 1–12 carbon atoms; and R is substituted alkyl, cycloalkyl or aryl, where a) substituted alkyl is a linear or branched, saturated or unsaturated hydrocarbon chain containing from 1–12 carbon atoms substituted with one or more substituents selected from the group consisting of: aryloxy, alkoxy, acyloxy, amino, N-acylamino, nitro, cyano, oxo, halogen, —C(O)OR⁶ and —S(O)$_n$R⁵, where $R^6$ is hydrogen or alkyl, n is 0–2 and $R^5$ is hydrogen, cycloalkyl, C₆–C₁₂aryl, substituted cycloalkyl, substituted C₆–C₁₂aryl, alkyl or alkyl substituted with one or more substituents selected from the group consisting of: alkoxy, acyloxy, amino, N-acylamino, oxo, hydroxy, cycloalkyl, substituted cycloalkyl, aryloxy, —C(O)OR⁶, —S(O)$_n$R⁷, nitro, cyano, halogen, C₆–C₁₂aryl, substituted C₆–C₁₂aryl and protected —OH, where $R^6$ is hydrogen or alkyl, n is 0–2 and $R^7$ is hydrogen or alkyl;

b) cycloalkyl is nonaromatic, unsaturated or saturated, cyclic or polycyclic C₃–C₁₂, optionally substituted with one or more substituents selected from the group consisting of: aryloxy, aryl, alkyl, alkoxy, acyloxy, cycloalkyl, substituted cycloalkyl, amino, N-acylamino, nitro, cyano, oxo, hydroxy, halogen, —C(O)OR⁶, —S(O)$_n$R⁵, protected —OH and alkyl substituted with one or more substituents selected from the group consisting of: alkoxy, acyloxy, C₆–C₁₂aryl, substituted C₆–C₁₂aryl, amino, N-acylamino, oxo, hydroxy, cycloalkyl, substituted cycloalkyl, —C(O)OR⁶, —S(O)$_n$R⁷, aryloxy, nitro, cyano, halogen and protected —OH, where $R^6$ is hydrogen or alkyl, n is 0–2, $R^7$ is hydrogen or alkyl and $R^5$ is hydrogen, cycloalkyl, C₆–C₁₂aryl, substituted cycloalkyl, substituted C₆–C₁₂aryl, alkyl or alkyl substituted with one or more substituents selected from the group consisting of: alkoxy, acyloxy, cycloalkyl, substituted cycloalkyl, aryloxy, amino, N-acylamino, oxo, hydroxy, —C(O)OR⁶, —S(O)$_n$R⁷, nitro, cyano, halogen, C₆–C₁₂aryl, substituted C₆–C₁₂aryl and protected —OH, where $R^6$ is hydrogen or alkyl, n is 0–2 and $R^7$ is hydrogen or alkyl; and c) aryl is cyclic or polycyclic aromatic C₃–C₁₂, optionally substituted with one or more substituents selected from the group consisting of: aryloxy, cycloalkyl, substituted cycloalkyl, alkyl, C₆–C₁₂aryl, alkoxy, acyloxy, substituted C₆–C₁₂aryl, amino, N-acylamino, nitro, cyano, halogen, hydroxy, —C(O)OR⁶, —S(O)$_n$R⁵, protected —OH and alkyl substituted with one or more substituents selected from the group consisting of: alkoxy, acyloxy, C₆–C₁₂aryl, substituted C₆–C₁₂aryl, amino, N-acylamino, oxo, hydroxy, cycloalkyl, substituted cycloalkyl, —C(O)OR$^6$, —S(O)$_n$R$^7$, aryloxy, nitro, cyano, halogen and protected —OH, where R$^6$ is hydrogen or alkyl, n is 0–2, R$^7$ is hydrogen or alkyl and R$^5$ is hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, aryloxy, amino, N-acylamino, oxo, hydroxy, —C(O)OR$^6$, —S(O)$_n$R$^7$, nitro, cyano, cycloalkyl, substituted cycloalkyl, halogen, C$_6$–C$_{12}$aryl, substituted C$_6$–C$_{12}$aryl and protected —OH, where R$^6$ is hydrogen or alkyl, n is 0–2 and R$^7$ is hydrogen or alkyl; and pharmaceutically acceptable salts, hydrates, solvates and esters thereof.

2. A compound of claim 1 of the Formula

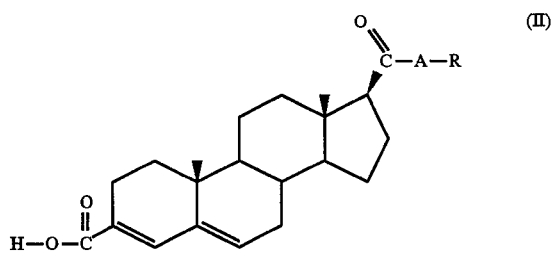

(II)

in which A and R are as defined in claim 1; and pharmaceutically acceptable salts, hydrates, solvates and esters thereof.

3. A compound of claim 2 in which A is a linear or branched, saturated or unsaturated hydrocarbon chain containing from 1–6 carbon atoms and R is a) a linear or branched, saturated or unsaturated hydrocarbon chain containing 1–12 carbon atoms substituted with one or more substituents selected from the group consisting of: —OC$_6$–C$_{12}$aryl, —OC$_1$–C$_4$alkyl, halogen, carboxy and —S(O)$_n$R$^7$, where n is 0–2 and R$^7$ is hydrogen or C$_{1-4}$alkyl;

b) C$_3$–C$_8$ nonaromatic, unsaturated or saturated, cycloalkyl, optionally substituted with one or more substituents selected from the group consisting of: —OC$_6$–C$_{12}$aryl, —(CH$_2$)$_m$OH, —OC$_1$–C$_4$alkyl, C$_6$–C$_{12}$aryl, C$_1$–C$_4$alkyl, trifluoromethyl, halogen, —(CH$_2$)$_p$COOH, —S(O)$_n$R$^7$ and protected —OH, where m is 0–4, p is 0–3, n is 0–2 and R$^7$ is hydrogen or C$_{1-4}$alkyl; or c) C$_4$–C$_{12}$aryl, optionally substituted with one or more substituents selected from the group consisting of: —OC$_6$–C$_{12}$aryl, —(CH$_2$)$_m$OH, C$_6$–C$_{12}$aryl, C$_1$–C$_4$alkyl, —OC$_1$–C$_4$alkyl, trifluoromethyl, halogen, —(CH$_2$)$_p$COOH, —S(O)$_n$R$^7$ and protected —OH, where m is 0–4, p is 0–3, n is 0–2 and R$^7$ is hydrogen or C$_{1-4}$alkyl; and pharmaceutically acceptable salts, hydrates, solvates and esters thereof.

4. A compound of claim 3 wherein A is a linear or branched, saturated or unsaturated hydrocarbon chain containing from 1–4 carbon atoms and R is a) a linear or branched, saturated or unsaturated hydrocarbon chain containing 1–6 carbon atoms substituted with one or more halogens;

b) C$_3$–C$_8$ nonaromatic, unsaturated or saturated cycloalkyl, optionally substituted with one or more substituents selected from the group consisting of: halogen, thio, methylsulfonyl, methylsulfoxyl, methylthio, carboxy, hydroxy, trifluoromethyl, phenoxy and methoxy or c) C$_4$–C$_{12}$aryl, optionally substituted with one or more substituents selected from the group consisting of: halogen, thio, methylsulfonyl, methylsulfoxyl, methylthio, carboxy, hydroxy, trifluoromethyl, phenoxy and methoxy and pharmaceutically acceptable salts, hydrates, solvates and esters thereof.

5. A compound of claim 4 wherein A is a linear or branched, saturated or unsaturated hydrocarbon chain containing from 1–4 carbon atoms and R is a) CF$_3$ b) C$_5$–C$_7$ cycloalkyl or c) C$_4$–C$_{12}$aryl, optionally substituted with one or more substituents selected from the group consisting of: halogen, thio, methylsulfonyl, methylsulfoxyl, methylthio, carboxy, hydroxy, trifluoromethyl, phenoxy and methoxy and pharmaceutically acceptable salts, hydrates, solvates and esters thereof.

6. A compound of claim 5 that is

17β-(phenylpropylcarbonyl)-androsta-3,5-diene-3-carboxylic acid,

17β-(benzylcarbonyl)-androsta-3,5-diene-3-carboxylic acid,

17β-(cyclohexylethylcarbonyl)-androsta-3,5-diene-3-carboxylic acid,

17β-(4-fluorophenethylcarbonyl)-androst-3,5-diene-3-carboxylic acid,

17β-(phenethylcarbonyl)-androst-3,5<diene-3-carboxylic acid,

17β-(5,5,5-trifluoro-1-oxopentyl)-androsta-3,5-diene-3-carboxylic acid,

17β-(2-cyclohexyl-1-oxoethyl)-androsta-3,5-diene-3-carboxylic acid,

17β-(3-methyl-3-phenyl-1-oxobutyl)-androsta-3,5-diene-3-carboxylic acid,

17β-(3-(4-methoxy phenyl)-1-oxopropyl)-androsta-3,5-diene-3-carboxylic acid,

17β-(3-(4-hydroxy phenyl)-1-oxopropyl)-androsta-3,5-diene-3-carboxylic acid or

17β-(2,6-difluorobenzylcarbonyl)-androsta-3,5-diene-3-carboxylic acid or pharmaceutically acceptable salts, hydrates, solvates and esters thereof.

7. A process for the preparation of a compound as claimed in claim 2, which process comprises reacting a compound of Formula

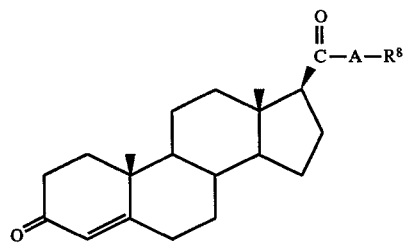

in which A is as described in claim 2 and R$^8$ is R as described in claim 2 with fluorosulfonic anhydride and a base, in a solvent, to form a compound of the formula

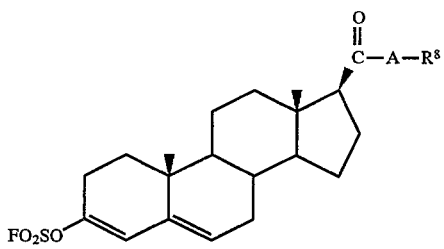

in which A and $R^8$ are as described above and subsequently reacting said compound in a metal-catalyzed coupling reaction in the presence of an appropriate coupling reagent followed by an optional hydrolysis reaction and thereafter optionally forming a pharmaceutically acceptable salt, hydrate or solvate thereof.

8. A compound of the formula

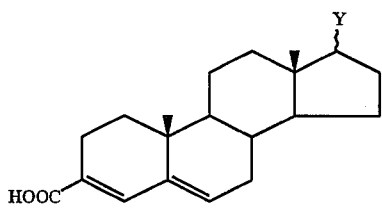

wherein
Y is α or β

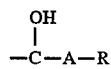

in which A and R are as defined in claim 1; and pharmaceutically acceptable salts, hydrates, solvates and esters thereof.

9. A compound of claim 8 in which the Y substituent is in the β position.

10. A compound of claim 8 in which the Y substituent is in the α position.

11. A pharmaceutical composition comprising a compound according to claim 1 and a pharmaceutically acceptable carrier.

12. A compound of the structure

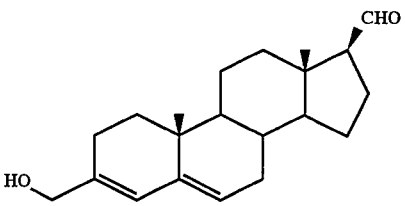

13. A method of inhibiting steroid 5-α-reductase activity in mammals which comprises administering to a subject in need thereof, an effective amount of a compound according to claim 1.

14. A method or reducing or maintaining prostate size in mammals which comprises administering to a subject in need thereof, an effective amount of a compound according to claim 1.

15. A method of treating prostatic adenocarcinoma in a subject which comprises administering to a subject in need thereof an effective amount of a compound of claim 1.

16. A method of treating baldness in a subject which comprises administering to a subject in need thereof an effective amount of a compound of claim 1.

17. A method of treating acne in a subject that comprises administering to a subject in need thereof an effective amount of a compound of claim 1.

18. A method of treating benign prostatic hypertrophy in a subject that comprises separate sequential or simultaneous administration of a compound according to claim 1 and an alpha-receptor antagonist compound.

19. A method of treating baldness in a subject that comprises separate sequential or simultaneous administration of a compound according to claim 1 and minoxidil.

* * * * *